United States Patent
Wechter et al.

(10) Patent No.: US 6,177,081 B1
(45) Date of Patent: *Jan. 23, 2001

(54) HUMAN AND MARMOSET ACTIVATING VIRUSES

(75) Inventors: Stephen R. Wechter, Houston; Luther E. Lindner, College Station, both of TX (US)

(73) Assignee: Pacific Biotech International, Inc., Houston, TX (US)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/901,128

(22) Filed: Jul. 28, 1997

Related U.S. Application Data

(63) Continuation of application No. 08/208,532, filed on Mar. 9, 1994, now abandoned.

(51) Int. Cl.⁷ .................................................... A61K 39/12
(52) U.S. Cl. .................................. 424/204.1; 424/184.1; 435/235.1
(58) Field of Search ........................ 435/5, 7.1; 530/350; 424/93.1

(56) References Cited

U.S. PATENT DOCUMENTS

| | | | |
|---|---|---|---|
| 4,692,403 | 9/1987 | Linder et al. | 435/5 |
| 4,816,395 | 3/1989 | Hancock et al. | 435/29 |

(List continued on next page.)

FOREIGN PATENT DOCUMENTS

| | | | |
|---|---|---|---|
| WO 92/20787 | 11/1992 | (WO) | C12N/7/02 |
| WO 93/10222 | 5/1997 | (WO) | C12N/7/00 |

OTHER PUBLICATIONS

Poiesz et al., "Detection and Isolation of Type C Retrovirus Particles from Fresh and Cultured Lymphocytes of a Patient with Cutaneous T–cell Lymphoma," Proc. Natl. Acad. Sci. USA 77(12):7415–7419, 1980.

(List continued on next page.)

*Primary Examiner*—Laurie Scheiner
*Assistant Examiner*—Jeffrey S. Parkin
(74) *Attorney, Agent, or Firm*—Benjamin Aaron Adler

(57) ABSTRACT

A novel family of lymphotropic viruses, designated activating viruses or AV, have been discovered and isolated from primates, including humans (HAV) and marmosets (MAV). These viruses are infectious in primates and are associated with a wide variety of symptoms including anemia, chronic rhinitis, diarrhea, emaciation, enteritis, and neurologic abnormalities. Virus was isolated and purified from the blood of wasting marmosets and humans. These viruses have the following characteristics: (1) a double-stranded DNA genome; (2) an average diameter of 100 nm as determined by electron microscopy; (3) a spherical capsid with imperfect icosahedral symmetry; (4) a buoyant density of 1.12–1.20 as determined by sucrose gradient centrifugation; (5) major antigens of 32, 44, 48, 58.8, and 106.5 kDa as determined by Western blot analysis and silver staining of SDS-PAGE-resolved proteins obtained from MAV- or HAV-infected OMK cell lysates; (6) minor antigens of 26, 30.5, 74.5, 80, 95, 126.8, 168, and 198 kDa as determined by Western blot analysis and silver staining of SDS-PAGE-resolved proteins obtained from MAV- or HAV-infected OMK cell lysates; (7) a replication deficiency in HELA, VERO, CCRF-CEM, MRC-5, WI-38, SW-13, SW-47, K562, RPMI-2650, Ramos, and NIH-3T3 cell lines as it applies to MAV; (8) replication competence in OMK cell cultures as it applies to both MAV and HAV; and (9) the absence of $Mg^{2+}$-dependent reverse transcriptase activity. The compositions of the claimed invention will prove useful in diagnostic assays.

5 Claims, 8 Drawing Sheets

U.S. PATENT DOCUMENTS

| | | | |
|---|---|---|---|
| 4,831,012 | 5/1989 | Estep | 514/6 |
| 4,831,118 | 5/1989 | Zimmerman et al. | 530/383 |
| 4,832,946 | 5/1989 | Green | 424/70 |
| 5,037,753 | 8/1991 | Pendersen et al. | 435/235.1 |
| 5,055,391 | 10/1991 | Montagnier et al. | 135/5 |
| 5,108,920 | 4/1992 | Ng et al. | 435/239 |

OTHER PUBLICATIONS

Marczynska et al., "Syncytium–Forming Virus of Common Marmosets (*Callithrix jacchus jacchus*)," Infect. Immun. 31(3):1261–1269, 1981.

Murphy, F., 1996, "Virus Taxonomy", in *Fields Virology*, Third Edition, Fields et al., eds., Lippincott–Raven Publishers, Philadelphia, pp. 15–57.

Nathanson, N., 1996, "Epidemiology", in *Fields Virology*, Third Edition, Fields et al., eds., Lippincott–Raven Publishers, Philadelphia, pp. 251–271.

Tyler et al., 1996, "Pathogenesis of Viral Infections", in *Fields Virology*, Third Edition, Fields et al., eds., Lippincott–Raven Publishers, Philadelphia, pp. 15–57.

Newman et al., 1995, "Immunological and Formulation Design Considerations for Subunit Vaccines", in *Vaccine Design: The Subunit and Adjuvant Approach*, Powell et al., eds., Plenum Press, New York, pp. 1–42.

Strongin, W., 1992, "Sensitivity, Specificity, and Predictive Value of Diagnostic Tests: Definitions and Clinical Applications", in *Laboratory Diagnosis of Viral Infections*, Lennette, ed., Marcel Dekker, Inc., New York, pp. 211–219.

Laufs and Steinke, "Vaccination of non–human primates against malignant lymphoma", *Nature*, vol. 253, pp. 70–72, 1975.

Johnson, et al., "Interaction of Herpesvirus Ateles and Herpesvirus Saimiri with Primate Lymphocytes", *Intervirology*, vol. 13, pp. 21–27, 1980.

Wright, et al., "Herpesvirus Saimiri: Protective Effect of Attenuated Strain Against Lymphoma Induction", *J. Cancer*, vol. 26, pp. 477–482, 1980.

Laufs and Melendez, "Oncogenicity of Herpesvirus Ateles in Monkeys", *J. Natl. Cancer Inst.*, vol. 51, pp. 599–608, 1973.

Deinhardt, et al., "Simian Herpesvirus", *Cancer Research*, vol. 33, pp. 1424–1426, Jun., 1973.

Laufs and Steinke, "Vaccination of Nonhuman Primates with Killed Oncogenic Herpesviruses", *Cancer Research*, vol. 36, pp. 704–705, Feb. 1976.

Lo, et al., "Fatal Infection of Silvered Leaf Monkeys with a Virus–Like Infectious Agent (VLIA) Derived From a Patient with AIDS", *Am. J. Trop. Med. Hyg.*, vol. 4, No. 40, pp. 339–409, 1989.

Daniel, et al., "Selective Antiviral Activity of Human Interferons on Primate Oncogenic and Neurotropic Herpesvirus", *Int. J. Cancer*, vol. 27, pp. 113–121, 1981.

Falk, et al., "Transformation of Marmoset Lymphocytes In Vitro with *Herpesvirus Ateles*", *Int. J. Cancer*, vol. 21, pp. 652–657, 1978.

Melendez, Two New Herpesviruses From Spider Monkeys (*Ateles geoffroyi*), *Journal of the National Cancer Institute*, vol. 49, No. 1, pp. 233–237, Jul., 1972.

Wright, et al., "Susceptibility of Common marmosets (*Callithrix jacchus*) to Oncogenic an Attenuated Strains of Herpesvirus saimiri", *J. Natl. Cancer Inst.*, vol. 59, No. 5, pp. 1475–1478, Nov., 1977.

Fleckenstein and Desrosiers, "Herpesvirus saimiri and Herpesvirus Ateles", *New England Regional Primate Research Inst.*, pp. 253–332.

Deinhardt, et al., "Simian Herpesviruses and Neoplasia", Univ. Of Illinois Med. Ctr., pp. 167–205.

Daniel, et al., "Comparative Studies of Interferon and Three Antiviral Agents on Neurotropic and Oncogenic Herpesviruses", *Antimicrobial Agents and Chemotherapy*, vol. 18, No. 4, pp. 622–628, Oct., 1980.

Modrow and Wolf, "Characterization of Herpesvirus Ateles Structural Proteins", *Virology*, vol. 125, pp. 251–255, 1983.

Luetzeler, et al., "Ultrastructural Studies on the Replication of Herpes Virus Ateles–73 in Owl Monkey Kidney Cells", *Archives of Virology*, vol. 60, pp. 59–73, 1979.

Pearson and Davis, Immune Response to Monkeys to Lymphotrophic Herpesvirus Antigens, *Cancer Research*, vol. 36, pp. 688–691, Feb. 1976.

Deinhardt, et al., "Induction of Neoplasms by Viruses in Marmoset Monkeys", *J. Med. Prim.*, vol. 1, pp. 29–50, 1972.

Heberling, R., et al., Jul. 1987, "Serodiagnosis of Rabies by Dot Immunobinding Assay", *Journal of Clinical Microbiology*, vol. 25, No. 7, pp. 1262–1264.

Heberling, R., et al., Jun. 1987, "A Dot–Immunoblotting Assay on Nitrocellulose with Psoralen Inactivated Heresvirus simiae (B virus)", *Laboratory Animal Science*, pp. 304–308.

Heberling, R., et al., Jan. 1986, "Rapid Dot–Immunobinding Assay on Nitrocellulose for Viral Antibodies", *Journal of Clinical Microbiology*, vol. 23, No. 1, pp. 109–113.

Herberling, R., et al., Apr. 1988, "Dot Immunoblotting Assay Compared with Enzyme–Linked Immunosorbent Assay for Rapid and Specific Detection of Retrovirus Antibody Induced by Human or Simian Acquired Retrovirus", *Journal of Clinical Microbiology*, vol. 26, No. 4, pp. 765–767.

Brown, N., et al.,Aug. 13, 1988, "Fall in Human Herpesvirus 6 Seropositively with Age", Fox, J., et al., "Antibody to Human Herpesvirus 6 in HIV–1 Positive and Negative Homosexual Men", and Brambati, B., et al., "Prenatal Diagnosis at 6 Weeks", *The Lancet*, pp. 396–397.

Morse, S., 1989, "Emerging Viruses: Newly evolved viruses and known viruses in new hosts were the focus of a recent conference", *ASM News*, vol. 55, No. 7, pp. 358–360.

Hausen, H., Nov. 22, 1991, "Viruses in Human Cancers", *Science*, vol. 254, pp. 1167–1173.

Lo, S., 1989, "A novel Virus–Like Infectious Agent in Patients with AIDS," *Am. J. Trop. Med. Hyg.*, vol. 402, No. 2, pp. 213–226.

Marx, J., Feb. 24, 1989, "How DNA Viruses May Cause Cancer", *Science*, vol. 243, pp. 1012–1013.

Heberling, R., et al., 1986, "Dot Immunoblotting Assay of Viral Antigen and Antibodies", *Development of Biological Standards*, vol. 64, pp. 199–203.

Kalter, S., et al., 1988, "The collection of blood on filter paper and its use in the dot–immunoblotting assay (DIA) for detection of antibody", in *Journal of Virological Methods*, vol. 20, pp. 181–183.

Radetsky, P., Sep. 1990, "Closing in on an AIDS Vaccine", *Discover*, pp. 71–77.

Rosenberg, Z., et al., Jul. 1990, "Activation of Latent HIV Infection", *The Journal of NIH Research*, vol. 2, pp. 41–45.

Felber, B., et al., Jan. 8, 1988, "A Quantitative Bioassay for HIV-1 Based on Trans-Activation", *Science*, vol. 239, pp. 184–186.

Spiegelman, S., "The Presence and Clinical Implications of a Virus–related Breast Cancer", From *Viruses in Naturally Occurring Cancers*, Book B, Essex, M, et al., eds., Cold Spring Harbor Laboratory, 1980, pp. 1149–1167.

Nottay, N., "Molecular Variation of Type 1 Vaccine–Related and Wild Polioviruses during Replication in Humans", *Virology*, vol. 108, pp. 405–423, 1981.

Crowell, R., et al., "Specific Alterations of Coxsackievirus B3 Eluted from Hela Cells", *Journal of Virology*, vol. 8, No. 4, pp. 509–515, Oct. 1971.

McLaren, L., et al., "Defective Interfering Particles From Poliovirus Vaccine and Vaccine Reference Strains", *Virology*, vol. 60, pp. 579–583, 1974.

Chopra, H., et al., "Electron Microscopic Detection of Simian–type Virus Particles in Human Milk", *Nature New Biology*, vol. 243, pp. 159–160, May 30, 1973.

Todaro, C., et al., "Endogenous New World primate type C viruses isolated from owl monkey (*Aotys trivirgatus*) kidney cell line", *Proc. National. Acad. Sci.*, vol. 75, No. 2, pp. 1004–1008, Feb. 1978.

Moore, D., et al., "Type B Particles in Human Milk", *Texas Reports on Biology and Medicine*, vol. 27, No. 4, Winter 1969.

Martin, M., et al., "Identification and cloning of endogenous retroviral sequences present in human DNA", *Proc. Natl. Acad. Sci.*, vol. 78, No. 8, pp. 4892–4896, Aug. 1981.

Sarkar, N., "Type B Virus and Human Breast", *The Role of Viruses in Human Cancer*, vol. 1, Giraldo and Beth, eds., Elsevier North Holland, Inc, 1980.

Karpas, A., "Human Leukemia in Vitro and the Expression of a New Virus", *The Role of Viruses in Human Cancer*, vol. 1, Giraldo and Beth, eds., Elsevier North Holland, Inc, 1980.

Sarkar, N., "The Etiology of Human Breast Cancer: Related Viral and Non–Viral Antigen Expression in Mammary Tumors of Mice and Man", *The Role of Viruses in Human Cancer*, vol. 2, Giraldo and Beth, eds., Elsevier North Holland, Inc, 1984.

Spear, P., et al., "Proteins Specified by Herpes Simplex Virus", *Journal of Virology*, vol. 9, No. 1, pp. 143–159, Jan. 1972.

Spear, P., et al., "The Protein Specified by Herpes Simplex Virus", *Virology*, vol. 36, pp. 545–555, 1968.

Dimmock, N., et al., "Proteins Specified by Influenza Virus in Infected Cells: Analysis by Polyacrylamide Gel Electrophoresis of Antigens Not present in the Virus Particle", *J. Gen. Virol.*, vol. 5, pp. 499–509, 1969.

Takahashi, M., "Chickenpox Virus", *Advances in Virus Research*, vol. 28, Academic Press, Inc., 1983, pp. 285–297.

Francki, R., "Plant Rhabdoviruses", *Advances in Virus Research*, vol. 18, Academic Press, Inc., 1973, pp. 257–279.

Matsumoto, S., "Rabies Virus", *Advances in Virus Research*, vol. 16, Academic Press, Inc., 1972, pp. 257–265.

Callahan, R., "The Organization of Mouse Mammary Tumor Virus Related Sequences in Human Cellular DNA", *International Symposium: Retroviruses and Human Pathology*, Gallo, et al., eds., Humana Press, Clifton, New Jersey, 1985, pp. 319–331.

Roizman, B., Chapter 1, "The Family Herpesviridae: General Description, Taxonomy, and Classification", *The Herpesviruses*, vol. 1, Roizman, ed., Plenium Press, New York, p. 1–23.

Marczynska, B., "Syncytium–Formin Virus of Common Marmosets (*Callithrix jacchus jacchus*)", *Infection and Immunity*, vol. 31, No. 3, Mar. 1981, pp. 1261–1269.

Bilberfeld, P., et al., "Ultrastructural Characterization of a New Human B Lymphotropic DNA Virus (Human Herpesvirus 6) Isolated From Patients with Lymphoproliferative Disease", *JNCI*, vol. 79, No. 5, pp. 933–941, Nov. 1987.

Briggs, M., et al., "Age Prevalence of Antibodies to Human Herpesvirus 6", *The Lancet*, vol. 1, No. 8593, pp. 1058–1059, May 7, 1988.

Downing, R.G., et al., "Isolation of Human Lymphotropic Herpesviruses From Uganda", and Tedder, R. S., et al., "A Novel Lymphotropic Herpesvirus", *The Lancet*, vol. 2, No. 8555, pp. 390–392, Aug. 15, 1987.

Salahuddin, S. Z., et al., "Isolation of a New Virus, HBLV, in Patients with Lymphoproliferative Disorders", *Science*, vol. 234, pp. 596–601, Oct. 31, 1986.

Matthew, W.D., et al., "The Production of a Monoclonal Antibody That Blocks the Action of a Neurite Outgrowth––promoting Factor", *Cold Spring Harbor Symp. Quant. Biol. XLVIII*, pp. 625–631, 1983.

Mayer, M. M., et al., "The Purification of Poliomyelitis Virus as Studied by Complement Fixation", vol. 78, 1957.

Ginsberg, H.S., "Herpesviruses", *Virology*, Chapter 53, pp. 161–177.

"Picornaviruses", *Virology*, Chapter 54, pp. 194–206, 212–215.

"Oncogenic Viruses II: RNA–Containing Viruses (Retroviruses)", *Virology*, pp. 377–380.

"Tumor Viruses", *Basic Virology*, Chapter 8, Section 1, pp. 126–129.

Kalter, S. S., "Overview of Simian Viruses and Recognized Virus Diseases and Laboratory Support for the Diagnosis of Viral Infections", Chapter 46, and "Collection and Handling of Animal Specimens for Detection of Viral Infections", Appendix A.

Characterization of Herpesvirus ateles structural Proteins Modrow and Wolf, *Virology*, 125:251–255, 1983.

Simian Herpesviruses and Neoplasia Deinhardt, et al., Univ. of Illinois Med. Ctr., pp. 167–205.

Comparative Studies of Interferon and Three Antiviral Agents on Neurotropic and Oncogenic Herpesviruses Daniel, et al., *Antimicrobial Agents and Chemotherapy*, No.4, 18:622–628, Oct. 1980.

Ultrastructural Studies on the Replication of Herpes Virus Ateles–73 in Owl Monkey Kidney Cells Luetzeler, et al., *Archives of Virology*, 60:59–73, 1979.

Immune Response to Monkeys to Lymphotrophic Herpesvirus Antigens Pearson and Davis, *Cancer Research*, 36:688–691, Feb. 1976.

Induction of Neoplasms by Viruses in Marmoset Monkeys Dienhardt, et al., *J. Med. Prim*, 1:29–50, 1972.

Vaccination of non–human primates against malignant lymphoma Laufs and Steinke, *Nature*, 253:70–72, Jan. 3, 1975.

Interaction of Herpesvirus Ateles and Herpesvirus Saimiri with Primate Lymphocytes Johnson, et al., *Intervirology*, 13:21–27, 1980.

Herpesvirus Saimiri: Protective Effect of Attenuated Strain Against Lymphoma Induction Wright, et al., *J. Cancer*, 26:477–482, 1980.

Oncogenicity of Herpesvirus ateles in Monkeys Laufs and Melendez, *J. Natl. Cancer Inst.*, 51:599–608, 1973.

Simian Herpeviruses Deinhardt, et al., *Cancer Research*, 33;1424–1426, Jun. 1973.

Vaccination of Nonhuman Primates with Killed Oncogenic Herpesviruses Laufs and Steinke, *Cancer Research*, 36:704–706, Feb. 1976.

Fatal Infection of Silvered Leaf Monkeys with a Virus–Like Infectious Agent (VLIA) Derived From a Patient with Aids Lo, et al., *Am. J. Trop. Med. Hyg.* No.40, 4:399–409, 1989.

Selective Antiviral Activity of Human Interferons on Primate Oncogenic and Neurotropic Herpesviruses Daniel, et al., *Int. J. Cancer*, 27:113–121, 1981.

Transformation of Marmoset Lymphocytes In Vitro with *Herpesvirus ateles* Falk, et al., *Int. J. Cancer*, 21:652–657, 1978.

Two New Herpesviruses From Spider Monkeys (*Ateles geoffroyi*) Melendez, *Journal of the National Cancer Institute*, No.1, 49:233–237, Jul. 1972.

Susceptibility of Common Marmosets (*Callithrix jacchus*) to Oncogenic and Attenuated Strains of *Herpesvirus saimiri* Wright, et al., *J. Natl. Cancer Inst.*, No.5, 59:1475–1478, Nov. 1977.

*Herpesvirus saimiri* and *Herpesvirus ateles* Fleckenstein and Desrosiers, *New England Regional Primate Research Inst.* pp. 253–332.

HUMAN AND MARMOSET ACTIVATING VIRUSES

This is a continuation of application Ser. No. 08/208,532, filed Mar. 9, 1994, now abandoned.

BACKGROUND OF THE INVENTION

1. Field of the Invention

The present invention relates generally to the detection and treatment of viral infection. More particularly, the invention relates to compositions and methods useful for the diagnosis of and vaccination against infection with a newly-discovered family of lymphotropic viruses designated activating virus (AV).

2. Description of Related Art

Viruses can contribute to the development of human tumors by a variety of mechanisms ranging from genetic stimulation of proliferation in host cells to induced immunosuppression that permits emergence of tumors not directly related to the suppressing virus. For instance, a patient infected with human immunodeficiency virus (HIV) has substantially increased risk for developing Kaposi sarcomas and B cell lymphomas, apparently due to immunosuppression caused by the HIV infection. Herpes simplex virus (HSV), on the other hand, has been suspected of contributing to tumors, particularly anogenital and oral cancers (A. Nahmias, et al., *Am. J. Epidemol.*, 91:547, 1970; W. E. Rawls, et al., *Cancer Res.*, 33:1542, 1973; R. Duff, et al., *J. Virol.*, 8:469, 1971; H. zur Hausen, *Int. Rev. Exp. Pathol*, 25:307, 1983).

Epstein-Barr virus (EBV), hepatitis B virus, several types of papilloma viruses, and HTLV-I and possibly II (human T-cell leukemia-lymphoma virus) are consistently linked to specific malignancies, but none of these viruses has been shown to be sufficient alone to induce cancer. Recent studies suggest that the Epstein-Barr and human papilloma viruses carry genes that immortalize infected cells and cause them to divide continuously. Evidence points to two genes, designated E6 and E7, as the likely transforming genes of the cancer-associated papilloma viruses. Both genes are consistently found in the DNA of cervical cancer cells, for example, and are active there. The Epstein-Barr virus also appears to carry a transforming gene, EBNA-2, that may stimulate the expression of other viral and cellular genes, including the latent membrane protein gene. Hepatitus B virus does not carry transforming genes so far as is known, yet it leads to liver cancer, perhaps because the viral DNA inserts itself into the genome of infected cells, activating a cellular oncogene.

Despite their significance, no DNA tumor virus can cause cancer by itself. Other changes and causative factors presently unidentified, perhaps several, are also required in infected cells. The present invention discloses a newly discovered virus called the "Activating Virus" or AV. This virus is implicated as a causative factor in a variety of cancers. It has been isolated from a wide variety of cancerous cells, many of which cancers have heretofore been thought to be linked to viral infection as an instigating factor, but where no viral etiologic agent has been found.

SUMMARY OF THE INVENTION

Compositions and methods are provided for detection of and vaccination against a novel virus designated activating virus (AV). The compositions include the whole virus and portions thereof, particularly including polypeptides which are cross-reactive with antibodies specific for determinant sites characteristic of the virus, such as those found on the major envelope and core proteins. The compositions further include antibodies capable of reacting with the virus and polynucleotides which are capable of duplexing with the AV genome.

Using the compositions of the present invention, the virus and viral infection may be detected by a variety of techniques, particularly immunoassays and techniques employing nucleotide probes. Immunoassays provide for the detection of the virus or antibody to the virus in a physiological specimen, particularly blood and lymph tissue. Nucleic probes are used to detect the presence of the AV genome in a physiological specimen. Vaccines may be prepared from the whole virus, either by partial or complete inactivation. Alternatively, subunit vaccines may be prepared from antigenic portions of the viral proteins capable of modulating B-lymphocyte or T-lymphocyte responses.

DESCRIPTION OF THE SPECIFIC EMBODIMENTS

Figure 1:
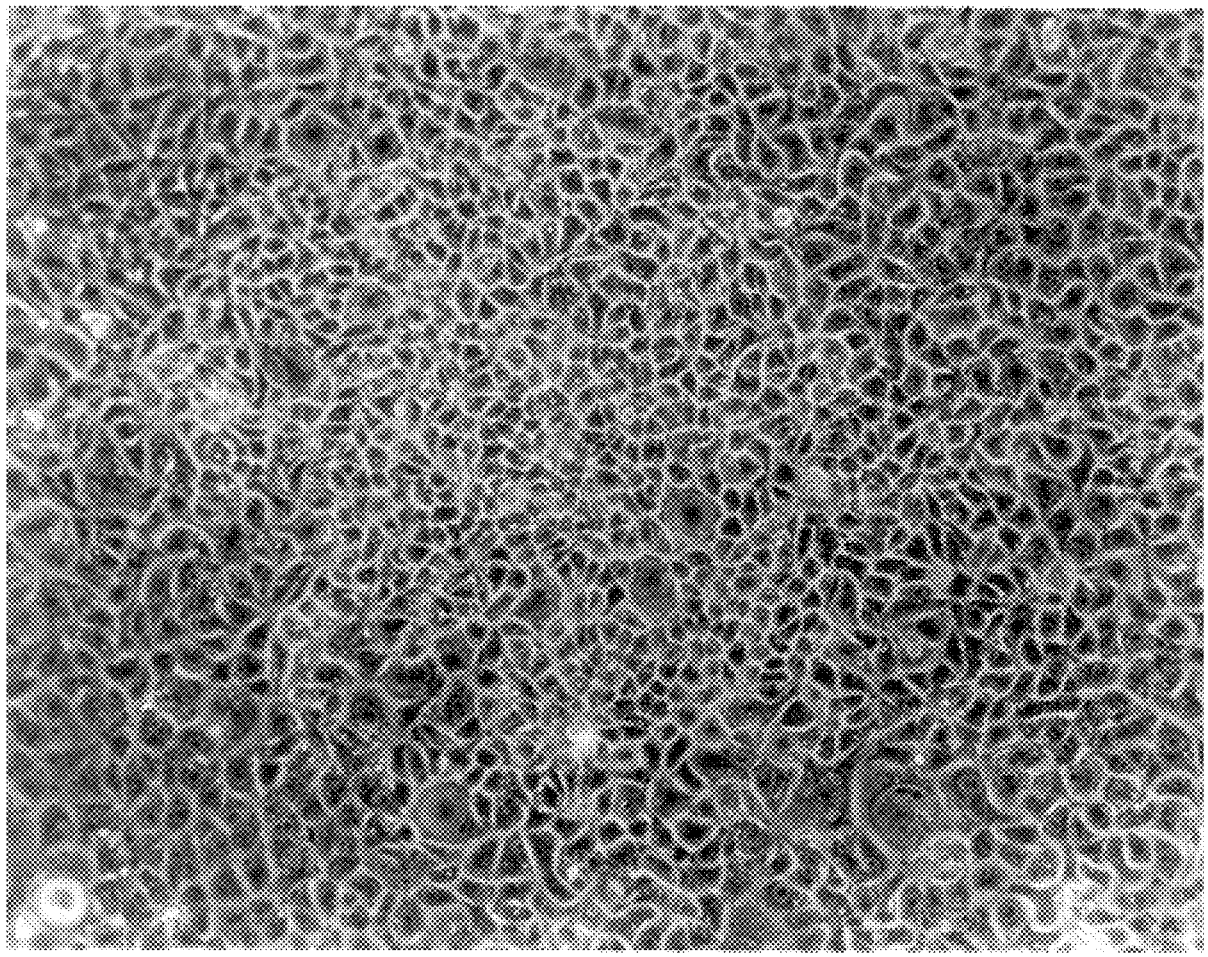
FIG. 1 is a photograph by phase contrast microscopy showing OMK cells inoculated with MAV after days 5–7.

A novel virus designated activating virus (AV) has been discovered and isolated in substantially pure form from primates such as humans (HAV) and marmosets (MAV). The virus is infectious in primates and is associated with a wide variety of symptoms, including alopecia, anemia, chronic rhinitis, diarrhea, emaciation, enteritis, gingivitis, neurologic abnormalities, periodontitis, and seborrheic dermatitis.

The etiology, pathogenesis, and morphology of AV do not resemble those of human immunodeficiency virus (HIV) and simian T-lymphotropic virus III (SIV), which cause acquired immunodeficiency syndrome in humans and primates, respectively. AV does not appear to be antigenically related to HIV or to SAIDS, or any other known virus. Preliminary surveys suggest that AV infection may be widespread, possibly accounting for a significant portion of various pathologies.

AV is a virus characterized as a double stranded DNA virus which morphologically has a smooth envelope, an average size slightly less than 100 nanometers, with a poorly defined capsid having spherical, imperfect icosahedral symmetry. The virus is also characterized by horizontal transmission, and may further be characterized by vertical transmission in at least some cases.

It is expected that AV is polymorphic, and reference to AV in the present application encompasses the entire AV family, including a variety of strains that share substantial amino acid sequence and nucleotide sequence homology and which are immunologically related. The information provided herein although derived from only a few strains of AV is sufficient to allow a viral taxonomist to identify other strains that fall within the scope of the claims.

Substantial amino acid sequence homology means at least about 75% homology, usually at least about 80% homology, and frequently 90% homology and above is found in at least some of the viral genes and proteins. For example, the viral proteins may display the requisite homology, while the genome as a whole does not. In such cases, so long as the viruses are immunologically related, the viruses will be considered to be an AV within the scope of the present invention.

The techniques for determining amino acid sequence homology are known in the art. For example, the amino acid sequence may be determined directly and compared to the sequences provided herein. For example also, the nucleotide sequence of the genomic material of the putative AV may be determined (usually via a cDNA intermediate); the amino acid sequence encoded therein can be determined, and the corresponding regions compared.

As used herein, a polynucleotide "derived from" a designated sequence, for example, the AV DNA or from an AV genome, refers to a polynucleotide sequence which is comprised of a sequence of at least 8 nucleotides, preferably at least 10–12 nucleotides, and even more preferably at least 15–20 nucleotides corresponding, homologous to or complementary to, a region of the designated nucleotide sequence. Preferably, the sequence of the region from which the polynucleotide is derived is homologous to or complementary to a sequence which is unique to an AV genome. Whether or not a sequence is unique to the AV genome can be determined by techniques known to those of skill in the art. For example, the sequence can be compared to sequences in databanks, e.g., Genebank, to determine whether it is present in the uninfected host or other organisms. The sequence can also be compared to the known sequences of other viral agents, including those which are known to induce disease in humans. The correspondence or non-correspondence of the derived sequence to other sequences can also be determined by hybridization under the appropriate stringency conditions. Hybridization techniques for determining the complementarity of nucleic acid sequences are known in the art, and are discussed, for example, in Maniatis, et al. (1982). In addition, mismatches of duplex polynucleotides formed by hybridization can be determined by known techniques, including for example, digestion with a nuclease such as S1 that specifically digests single-stranded areas in duplex polynucleotides. Regions from which typical DNA sequences may be "derived" include but are not limited to, for example, regions encoding specific epitopes, as well as non-transcribed and/or non-translated regions.

The derived polynucleotide is not necessarily physically derived from the AV nucleotide sequence, but may be generated in any manner, including for example, chemical synthesis or DNA replication or transcription, which are based on the information provided by the sequence of bases in the region(s) from which the polynucleotide is derived. In addition, combinations of regions corresponding to that of the designated sequence may be modified in ways known in the art to be consistent with an intended use.

Similarly, a polypeptide or amino acid sequence derived from a designated nucleic acid sequence refers to a polypeptide having an amino acid sequence identical to that of a polypeptide encoded in the sequence, or a portion thereof wherein the portion consists of at least 3–5 amino acids, and more preferably at least 8–10 amino acids, and even more preferably at least 11–15 amino acids, or which is immunologically identifiable with a polypeptide encoded in the sequence.

A recombinant or derived polypeptide is not necessarily translated from a designated nucleic acid sequence or from an AV genome; it may be generated in any manner, including for example, chemical synthesis, or expression of a recombinant expression system, or isolation from mutated AV.

The term "recombinant polynucleotide" as used herein intends a polynucleotide of genomic DNA, semisynthetic, or synthetic origin which, by virtue of its origin or manipulation: (1) is not associated with all or a portion of the polynucleotide with which it is associated in nature or in the form of a library; and/or (2) is linked to a polynucleotide other than that to which it is linked in nature.

The term "polynucleotide" as used herein refers to a polymeric form of nucleotides of any length, either ribonucleotides or deoxyribonucleotides. This term refers only to the primary structure of the molecule. Thus, this term includes double- and single-stranded DNA, as well as double- and single stranded RNA. It also includes modified, for example, by methylation and/or by capping, and unmodified forms of the polynucleotide.

As used herein, the term "AV containing a sequence corresponding to a cDNA" means that the HCV contains a polynucleotide sequence which is homologous to or complementary to a sequence in the designated DNA; the degree of homology or complementarity to the cDNA will be approximately 50% or greater, will preferably be at least about 70%, and even more preferably will be at least about 90%. The sequences which correspond will be at least about 70 nucleotides, preferably at least about 80 nucleotides, and even more preferably about 90 nucleotides in length. The correspondence between the AV sequence and the cDNA can be determined by techniques known in the art, including, for example, a direct comparison of the sequenced material with the cDNAs described, or hybridization and digestion with a single strand nucleases, followed by size determination of the digested fragments. Techniques for purifying viral polynucleotides from viral particles are known in the art, and include for example, disruption of the particle with a chaotropic agent, and separation of the polynucleotide(s) and polypeptides by ion-exchange chromatography, affinity chromatography, and sedimentation according to density.

"Immunologically related" means that the various strains will display substantial serologic cross-reactivity with the newly-discovered strains which have been deposited. Serologic cross-reactivity is defined as the ability of an antiserum or antibodies specific for the deposited AV strains to react with other AV strains as well as the deposited strains. Usually, immunologically related strains will cross-react with antibodies specific for more than one epitopic site, usually more than five epitopic sites, and frequently ten or more epitopic sites.

Conveniently, AV strains may be identified by Western blot analysis where purified virus is disrupted with a suitable detergent (e.g., sodium dodecyl sulfate) and separated on a slab gel by electrophoresis. The separated polypeptide bands are transferred from the gel to nitrocellulose filter paper and visualized with labelled antibody. The molecular weights of the various resolved bands may then be determined by comparison to known molecular weight standards. Substantial similarity between the Western blot analysis of an unidentified virus and that of a known AV virus, when prepared using the same technique, indicates that the unknown virus is likely an AV virus.

AV bands obtained by Western blot analysis cover a density range of 1.12–1.20 g/cm$^3$ (30–45% sucrose). Western blotting of AV-infected cell lysate yields major bands at 32 kD, 44 kD, 48 kD, and 58.8 kD, respectively. A distinct band was seen at 106.5 kD, with faint bands seen at 26 kD, 30.5 kD, 74.5 kD, 80 kD, 95 kD, 126.8 kD, 168 kD, and 198 kD, respectively.

AV may be isolated from the sera of infected animals by conventional techniques. For example, peripheral blood lymphocytes (PBL) may be isolated from the blood of infected animals and placed in suitable culture media. A cytopathic effect (CPE) as described in Example 1 below, is also seen when owl monkey kidney cells, (ATCC #CRL 1556) are inoculated with viremic human or marmoset serum. The cultures are incubated, with normal PBL's being periodically introduced to the culture in order to maintain its viability as the original cells are killed by the virus. The infected cells should be placed in fresh culture medium periodically, and the virus may be recovered from the supernatant of the cell culture by sucrose-gradient separation, or other known separation techniques.

AV may also be obtained from other specimens, particularly from the lymph tissues of infected animals. The lymph tissues are broken and then suspended in culture medium, and the procedures described above are then carried out. From the isolated virus the DNA and/or cDNA encoding the virus, and portions thereof, can be derived using methods known in the art.

Compositions according to the present invention include the whole virus, as well as portions of the virus. The whole virus may be maintained in in vitro culture, as described above, or may be viably frozen at −85° C., or below about −78° C. (solid $CO_2$-dry ice), usually in the presence of agents which promote amorphous, vitreous solidification rather than crystallization. Suitable agents include glycerol and dimethylsulfoxide. Portions of AV of particular interest include the structural and regulatory proteins encoded by the AV genome, including the capsid and core proteins, and fragments thereof.

Polypeptides of the present invention will be either haptenic or antigenic, including at least six amino acids, usually at least nine amino acids, and more usually twelve or more amino acids found contiguously within one of the natural AV proteins. Polypeptides will generally correspond to at least one epitopic site which is characteristic of AV, preferably to epitopes associated with B and/or T cells. The term "characteristic" in this context means that the epitopic site will allow immunologic detection of the virus in a physiological sample with reasonable assurance. Usually, it will be desirable that the epitopic site be immunologically distinct from (i.e., not cross-reactive with antibodies which recognize) viruses other than AV. In some cases, however, it may be desirable that the epitopic site be immunologically similar to other viruses.

The AV polypeptides may be natural, i.e., including the entire AV protein or fragments thereof isolated from a natural source, or may be synthetic. The natural polypeptides may be isolated from the whole virus which is obtained as described above by conventional techniques, such as affinity chromatography. Conveniently, polyclonal or monoclonal antibodies obtained according to the present invention may be used to prepare a suitable affinity column by well-known techniques. Such techniques are taught, for example, in Hudson and Hay, Chapter 8, *Practical Immunology,* Blackwell Scientific Publications, Oxford, United Kingdom, 1980.

Synthetic polypeptides which are immunologically cross-reactive with a natural AV protein may be produced by either of two general approaches. First, polypeptides having fewer than about 80 amino acids, and typically fewer than about 50 amino acids, may be synthesized by the well-known Merrifield solid-phase synthesis method where amino acids are sequentially added to a growing chain (Merrifield, *J. Am. Chem. Soc.,* 85:2149–2156, 1963).

The second and preferred method for synthesizing the polypeptides of the present invention involves the expression in cultured cells of recombinant DNA molecules encoding a desired portion of the AV genome. The portion of the AV genome may itself be natural or synthetic, with natural genes obtainable from the isolated virus by conventional techniques. Polynucleotides may be synthesized by well-known techniques. For example, short single-stranded DNA fragments may be prepared by the phosphoramidite method (Beaucage and Carruthers, *Tet. Letters,* 22:1859–1862, 1981). Double-stranded fragments may then be obtained either by synthesizing the complementary strand and then annealing the strands together under appropriate conditions, or by adding the complementary strand using DNA polymerase with an appropriate primer sequence.

The natural or synthetic DNA fragments coding for the desired AV protein or fragment may be incorporated in a DNA construct capable of introduction into and expression in in vitro cell culture. Usually, the DNA constructs will be suitable for replication in a unicellular host, such as yeast or bacteria. They may also be intended for introduction and integration within the genome of cultured mammalian or other eukaryotic cells. DNA constructs prepared for introduction into bacteria or yeast will include a replication system recognized by the host, the AV DNA fragment encoding the desired polypeptide product, transcriptional and translational initiation regulatory sequences joined to the 5'-end of the AV DNA fragment, and transcriptional and translational termination regulatory sequences joined to the 3'-end of the fragment. The transcriptional regulatory sequences will include a heterologous promoter that is recognized by the host. Conveniently, a variety of suitable expression vectors are commercially available for a number of hosts.

To be useful in the detection methods of the present invention, the polypeptides are obtained in a substantially pure form, that is, typically from about 50% W/W or more purity, substantially free of interfering proteins and contaminants. Preferably, the AV polypeptides are isolated or synthesized in a purity of at least 80% W/W, and more preferably, in at least about 95% W/W purity. Using conventional protein purification techniques, homogeneous polypeptide compositions of at least about 99% W/W purity can be obtained. For example, the proteins, and even intact AV, may be purified by use of the antibodies described hereinafter using the immunoabsorbant affinity columns described hereinabove.

Once a sufficient quantity of AV polypeptides have been obtained, polyclonal antibodies specific for AV may be produced by in vitro or in vivo techniques. In vitro techniques involve in vitro exposure of lymphocytes to the antigenic polypeptides, while in vivo techniques require the injection of the polypeptides into a wide variety of vertebrates. Suitable vertebrates are non-human, including mice, rats, rabbits, sheep, goats, donkeys, and the like. Donkeys and other equine species are preferred for generation of the antibodies of this invention. Polypeptides having more than about thirty amino acids, usually more than about fifty amino acids, may serve directly as the immunogen. If the polypeptide is smaller than about 10 kD, particularly less than about 6kD, it may be necessary to join the polypeptide to a larger molecule to elicit the desired immune response. The immunogens are then injected into the animal according to a predetermined schedule, and the animals are bled periodically with successive bleeds having improved titer and specificity. Injections may be made intramuscularly, subcutaneously, or the like, and an adjuvant, such as incomplete Freund's adjuvant, will usually be employed. The whole virus can also be used as the immunogen, although selection of antibodies specific for a particular determinant will be more difficult.

If desired, monoclonal antibodies can be obtained by preparing immortalized cell lines capable of producing antibodies having the desired specificity. Such immortalized cell lines may be produced in a variety of ways. Conveniently, a small vertebrate, such as a mouse, is hyper-immunized with the desired antigen by the method just described. The vertebrate is then killed, usually several days after the final immunization, the spleen removed, and the spleen cells immortalized. The manner of immortalization is not critical. Presently, the most common technique is fusion with a myeloma cell fusion partner, as first described by Kohler and Milstein, *Eur. J. Immunol.*, 6:511–519, 1976. Other techniques include EBV transformation, transformation with oncogenes, and transformation with retroviruses, or any other method which provides for stable maintenance of the cell line and production of monoclonal antibodies.

When employing fusion with a fusion partner, the manner of fusion is not critical and various techniques may be employed. Conveniently, the spleen cells and myeloma cells are combined in the presence of a non-ionic detergent, usually polyethylene glycol, and other additives such as Dulbecco's Modified Eagle's medium, for a few minutes. At the end of the fusion, the non-ionic detergent is rapidly removed by washing the cells. The fused cells are promptly dispensed in small culture wells (usually in a microtiter plate at relatively low density, ranging from about one to $5 \times 10^5$ cells/well), in a selective medium chosen to support growth of the hybrid cells while being lethal to the myeloma cells. Usually, the myeloma cell line has been mutated to be sensitive, and the medium includes a HAT concentration sufficient to inhibit the proliferation of the unfused myeloma cells.

After sufficient time, usually from about one to two weeks, colonies of hybrids are observed and plates containing hyperpositive wells are identified. The plates and wells having only one colony per well are selected, and supernatants from these wells are tested for binding activity against AV or a particular AV protein. Once positive hybridomas are identified, the cell line can be maintained as a viable culture and/or a quantity of the virus may be grown out, separated, and stored by lyophilization.

Depending on the desired use for the antibodies, further screening of the hybridomas may be desirable. For use in immunodiagnostic assays, antibodies having very high specificity and affinity for the antigenic site of an AV, or an AV polypeptide of this invention are desirable.

Once the desired hybridomas have been selected, monoclonal antibodies may be isolated from supernatants of the growing colonies. The yield of antibodies obtained, however, is usually low. The yield may be enhanced by various techniques, such as injection of the hybridoma cell line into the peritoneal cavity of a vertebrate host. Monoclonal antibodies may then be harvested from the ascites fluid or the blood. Proteinaceous and other contaminants will usually be removed from the monoclonal antibodies prior to use by conventional techniques, e.g., chromatography, gel filtration, precipitation, extraction, or the like.

Alternatively cDNA encoding the antibody chains can be obtained by known methods and prokaryotic or eukaryotic host cells can be transformed with vectors containing the cDNA to produce the anti-AV antibodies recombinantly. The preferred host cells are owl monkey kidney cells (OMK), for instance those provided by ATCC #CRL 1556.

The polypeptides and antibodies of the present invention may be used with or without modification for the detection of or vaccination against AV infection. Frequently, the polypeptides and antibodies will be labelled by joining, either covalently or non-covalently, a substance which provides for detectable signal. A wide variety of labels and conjugation techniques are known and are reported extensively in both the scientific and patent literature. Some of the labels include radionuclides, enzymes, substrates, cofactors, inhibitors, fluorescers, chemiluminescers, magnetic particles and the like. Patents teaching the use of such labels include U.S. Pat. Nos. 3,817,837; 3,850,752; 3,939,350; 3,996,345; 4,277,437; 4,275,149; and 4,366,241.

Antibodies and polypeptides prepared as described above can be used in various immunological techniques for detecting AV and anti-AV antibodies in physiological specimens, particularly body fluid samples, including blood, plasma, serum, urine, and the like, and cell samples, such as lymphocytes. Depending on the nature of the sample, both immunoassays and immunohistochemical staining techniques may find use.

Liquid phase immunoassays and Western blot analysis will find use in detection of AV in body fluids, particularly blood and urine. The use of antibodies in protein binding assays is well established. Numerous competitive and non-competitive protein binding assays have been described in the scientific and patent literature, and a large number of such assays are commercially available. Detailed methods for detecting the presence of the viruses in serum samples are set forth in the Experimental section. Additionally, enzyme linked immunosorbent assays (ELISA) for detecting presence of antibodies to AV in blood are also set forth in the Experimental section.

Compositions of the present invention are also useful in preparing vaccines for protection against AV infection. For example, the whole virus may be wholly or partially inactivated. Partial inactivation may be achieved by passage at elevated temperatures or by contact with mutagens, such as ultraviolet light, ethyl methanesulfonate, and the like. Complete inactivation may be achieved by contact with other agents, including formalin, phenol, α-lactoproprionate, ultraviolet light, heat, psoralens, platinum complexes, ozone and other viricidal agents.

Vaccination with live attenuated activating virus is also contemplated, preferably in combination with aluminum hydroxide or Freund's adjuvant in a non-toxic, prophylactic amount. An advantage of using attenuated live viral vaccine is the small amount of material necessary to generate a strong immune response. The virus can be attenuated using methods well known in the art. For instance the serial passage of live virus in African Green monkey kidney (AGMK) cells is described by L. N. Binn, *J. Clin. Microbiol.* 20:28–33, 1984. Alternatively, attenuated virus can be propagated in vitro in cell cultures as described in U.S. Pat. No. 5,021,348, which is incorporated herein by reference in its entirety. Briefly, the cell cultures are derived from fetal or newborn kidney cells from rhesus monkey (FRhK6), cynomolgus monkey, or cercopithecus monkey or diploid fibroblast cells derived from human or non-human primate lung tissue, WI-38 (ATCC #CCL 75) or MRC-5 (ATCC #CCL 171). The virus first is passed at least once and preferably from about 2 to about 20 times in the kidney or liver cell cultures and then at least 4 times, preferably from about 5 to about 20 times in diploid fibroblast cells derived from human lung tissue.

The inoculated cell culture is incubated for an extended period of time until positive results are obtained for the presence of the antigen, at least about 20 days, and preferably from about 25 up to about 100 days. The incubation is carried out in the presence of a nutrient medium that maintains the cells at temperatures permitting propagation of the virus in the cell culture, typically from about 30° to about 39°, preferably 35° C. The nutrient medium can be, for example, Eagle's Minimum Essential Medium (EMEM), Williams Medium E, Medium 199, Dulbecco's Modified Eagle's Medium, RPMI Media or Basal Medium Eagle with 0.5% fetal calf serum. The cultures are subsequently harvested and serial passages of the viral agent are carried out.

The protective effects of most vaccines are due to induced levels of circulating antibodies. Live attenuated viruses can also be incorporated into immunostimulating complexes (ISCOM) for use as a vaccine using methods well known in the art. Activating Virus immunostimulating complexes (ISCOM)-vaccine containing viral capsid proteins to raise high neutralization antibody titres after two booster doses in Balb/c CUM and A/J inbred mouse strains. Fohlman, et al., supra. The presentation of viral coat protein antigens in ISCOM particles has three main advantages: no replicating viral nucleic acid is introduced into the host, high levels of neutralizing antibodies are achieved, and a cellular immunity is evoked, including cytotoxic T-cells induced under restriction of MHC class II. The methodology for making ISCOM vaccines is well known in the art. (B. Morein, et al., *Nature,* 308:457–60, 1984).

Known techniques of molecular biology can be used to insert genes for antigenic epitopes into vectors. Vaccinia virus has been used as one such vector. See *Current Protocols in Molecular Biology,* Ed. by F. M. Ausubel, Current Protocols, Vol. 2, §16.17, 1993. Presently the genes for the capsid proteins of several Coxsackie B viruses are available and can be inserted into a suitable vector using techniques well known in the art.

In addition, liposomes, including unilamellar bodies comprising a single lipid bilayer, can be used as vectors to deliver viral proteins, such as viral coat proteins. Such methods are taught in U.S. Pat. No. 4,148,876 to Almeida, et al. and U.S. Pat. No. 4,663,161 to Mannino, et al., which are incorporated herein by reference in their entirety.

The viral proteins and portions thereof, prepared as described above, may also be used in the preparation of subunit vaccines prepared by known techniques. Polypeptides displaying antigenic regions capable of eliciting protective immune response are selected and incorporated in an appropriate carrier. Alternatively, an antigenic portion of a viral protein or proteins may be incorporated into a larger protein by expression of fused proteins. The preparation of subunit vaccines for other viruses is described in various references, including Lerner, et al., *Proc. Natl. Acad. Sci. USA,* 78:3403, 1981 and Bhatanagar, et al., *Proc. Natl. Acad. Sci. USA,* 79:4400, 1982. See also, U.S. Pat. No. 4,565,697 (where a naturally-derived viral protein is incorporated into a vaccine composition); U.S. Pat. Nos. 4,528,217 and 4,575,495 (where synthetic peptides forming a portion of a viral protein are incorporated into a vaccine composition). Other methods for forming vaccines employing only a portion of the viral proteins are described in U.S. Pat. Nos. 4,552,757; 4,552,758; and 4,593,002. The relevant portions of each of these patents are incorporated herein by reference. Such vaccines are useful for raising an immune response against AV, for example a protective antibody titer, in mammals susceptible to the virus, such as marmosets, donkeys and other equine species, and in humans. Since the activating virus is believed to function in the capacity of a helper agent contributing to development of many cancers attributed to viral and retroviral infections, it is believed that the raising of protective antibody titers against AV may serve as a prophylactic measure against development of such cancers as Kaposi sarcomas and B cell lymphomas, anogenital and oral cancers associated with Herpex Simplex Virus (HSV), Burkitt's lymphoma and nasopharyngeal cancer associated with Epstein-Barr virus (EBV), adult T cell leukemia associated with HTLV-I, and specific malignancies linked to hepatitis B virus, several types of papilloma viruses, and HTLV-I and possibly II (human T cell leukemia-lymphoma virus).

The vaccines prepared as described above may be administered in any conventional manner, including nasally, subcutaneously, or intramuscularly, except that nasal administration will usually not be employed with a partially inactivated virus vaccine. Adjuvants will also find use with subcutaneous and intramuscular injection of completely inactivated vaccines to enhance the immune response.

Diagnostic tests for detecting the presence of AV in biological samples may also be performed using polynucleotide probes. Such polynucleotide probes may be prepared based on the sequence of the viral genome. The length of the probe is not critical, but will usually comprise at least about 12 bases, more usually comprising at least about 16 bases, which are substantially complementary to a portion of the viral genome. The probe itself may be DNA or RNA, and the probe need not have perfect complementarity with the AV genome, with one or two mismatched pairs being acceptable for probes up to 20 bases in length and three to five mismatched pairs in probes from 20 to 35 bases. The probes may be prepared synthetically, with suitable synthetic techniques having been described above, and will include a detectable label. Usually, the synthetic sequences are expanded in commonly available cloning vectors and suitable hosts in order to obtain large quantities. The expanded vectors may themselves be labelled for use as probes, or shorter fragments containing complementary strands may be excised and labelled. Methods for the preparation and utilization of nucleotide probes for diagnostic testing are described in U.S. Pat. No. 4,358,535 to Falkow, et al., the disclosure of which is incorporated by reference.

A variety of labels have been employed, including those which have been described above for use in immunoassays, particularly radionuclides. Suitable labels may be bound to the probe by a variety of techniques. Commonly employed is nick translation with $\alpha$-$^{32}$P-dNTP terminal phosphate hydrolysis with alkaline phosphatase followed by 5'-end labelling with radioactive $^{32}$P employing $\gamma$-$^{32}$P-NTP and T4 polynucleotide kinase or 3'-end labelling with an $\alpha$-$^{32}$P-NTP and terminal deoxynucleotidyl transferase. Alternatively, nucleotides can be synthesized where one or more of the atoms present are replaced with a radioactive isotope, e.g., hydrogen with tritium. In addition, various linking groups can be employed. The terminal hydroxyl can be esterified with inorganic acids, e.g., $^{32}P$ phosphate or $^{14}C$ organic acids, or else esterified with bifunctional reagents to provide other reactive groups to which labels can be linked.

The following examples are offered by way of illustration, not by way of limitation.

EXAMPLE 1

Isolation and Purification of Marmoset Activating Virus (MAV)

Initial studies demonstrated that lymphocytes obtained from the blood of wasting marmosets could be maintained for substantial periods when stimulated with IL-2 (4 units/ml). A small percentage of lymphocytes were positive by immunoperoxidase staining with antibody from recovered waster marmosets. The reactivity was shown to persist for four months.

Figure 2:
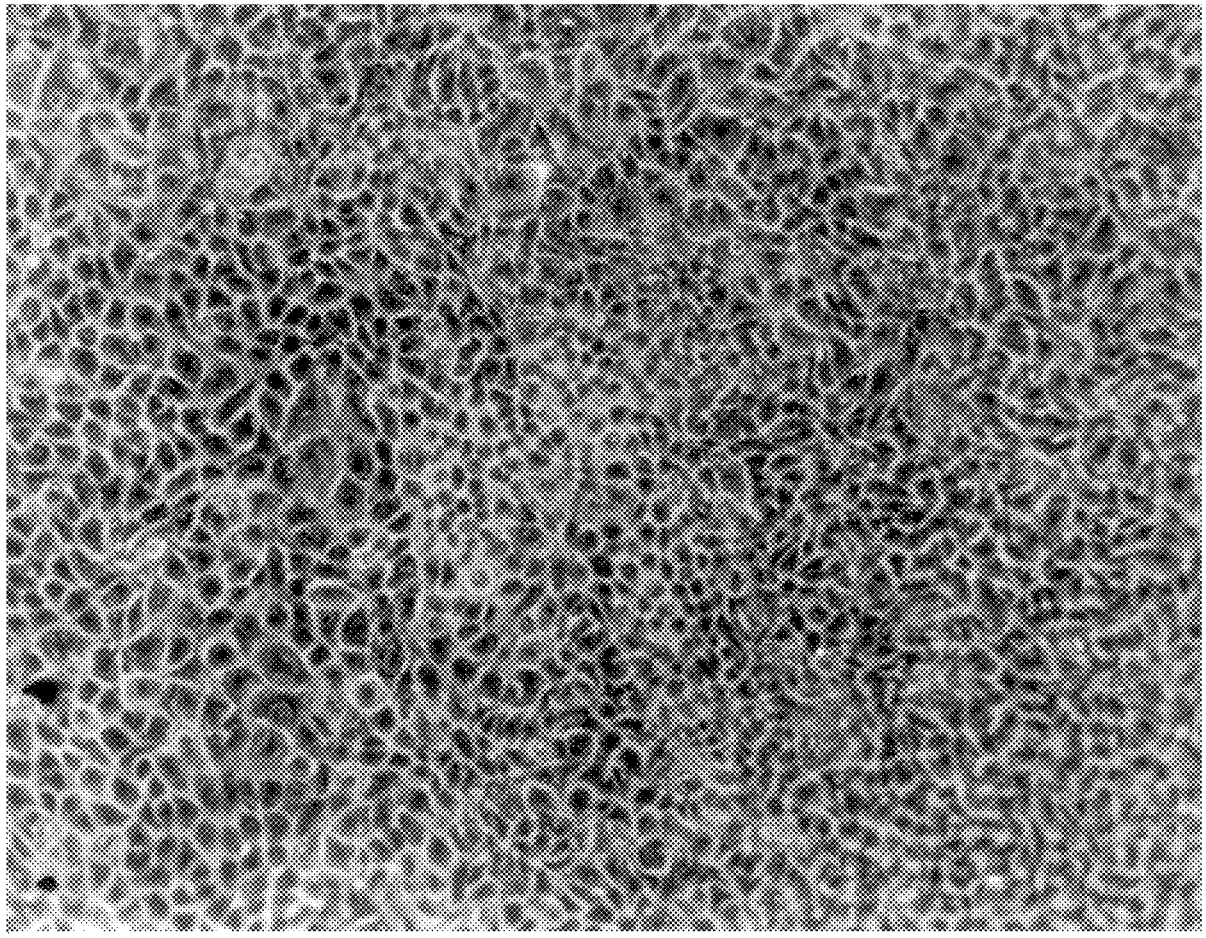
FIG. 2 is a photograph by phase contrast microscopy showing OMK cells inoculated with MAV after days 5–7.
Figure 3:
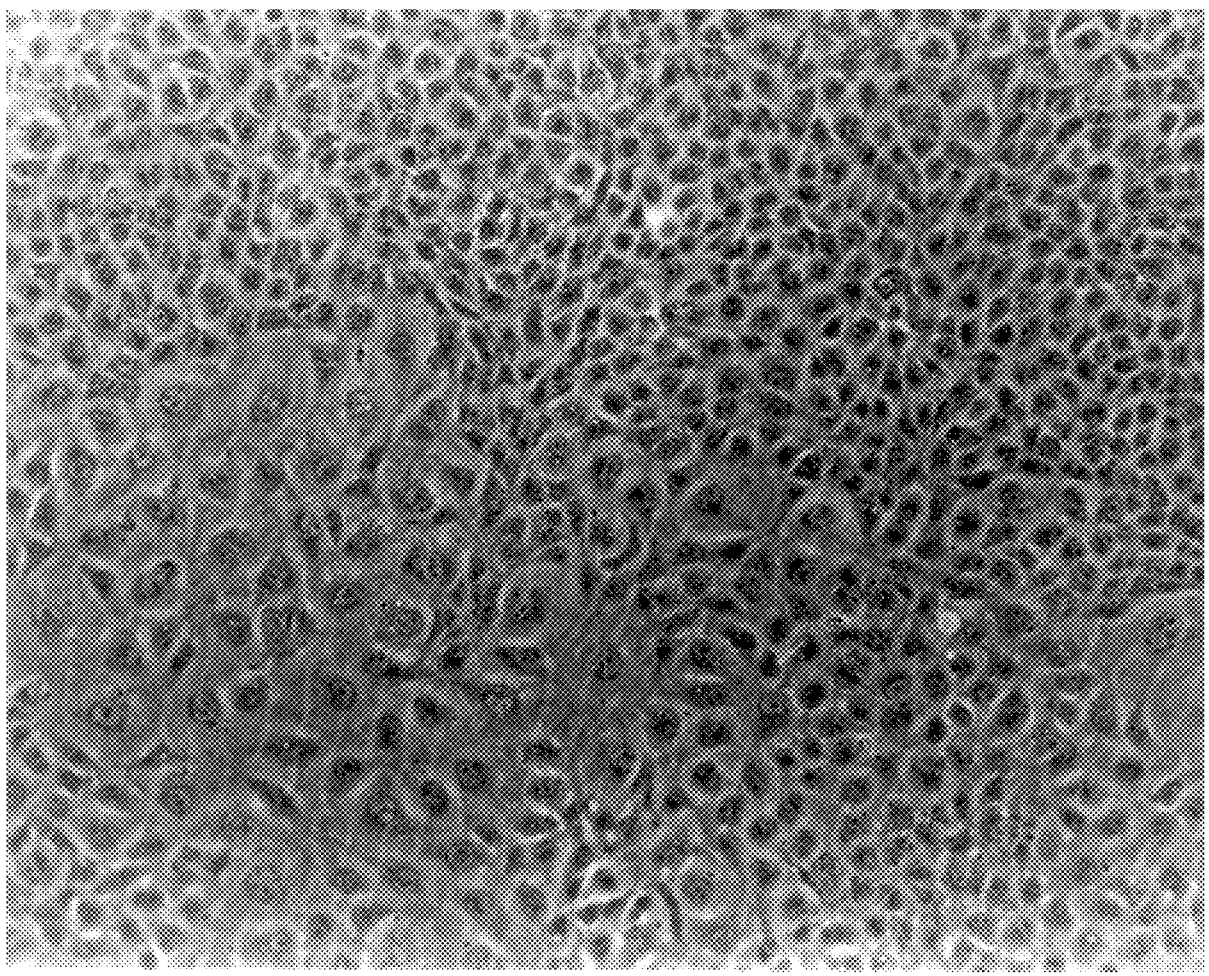
FIG. 3 is a photograph by phase contrast microscopy showing uninfected OMK cells.
Figure 4:
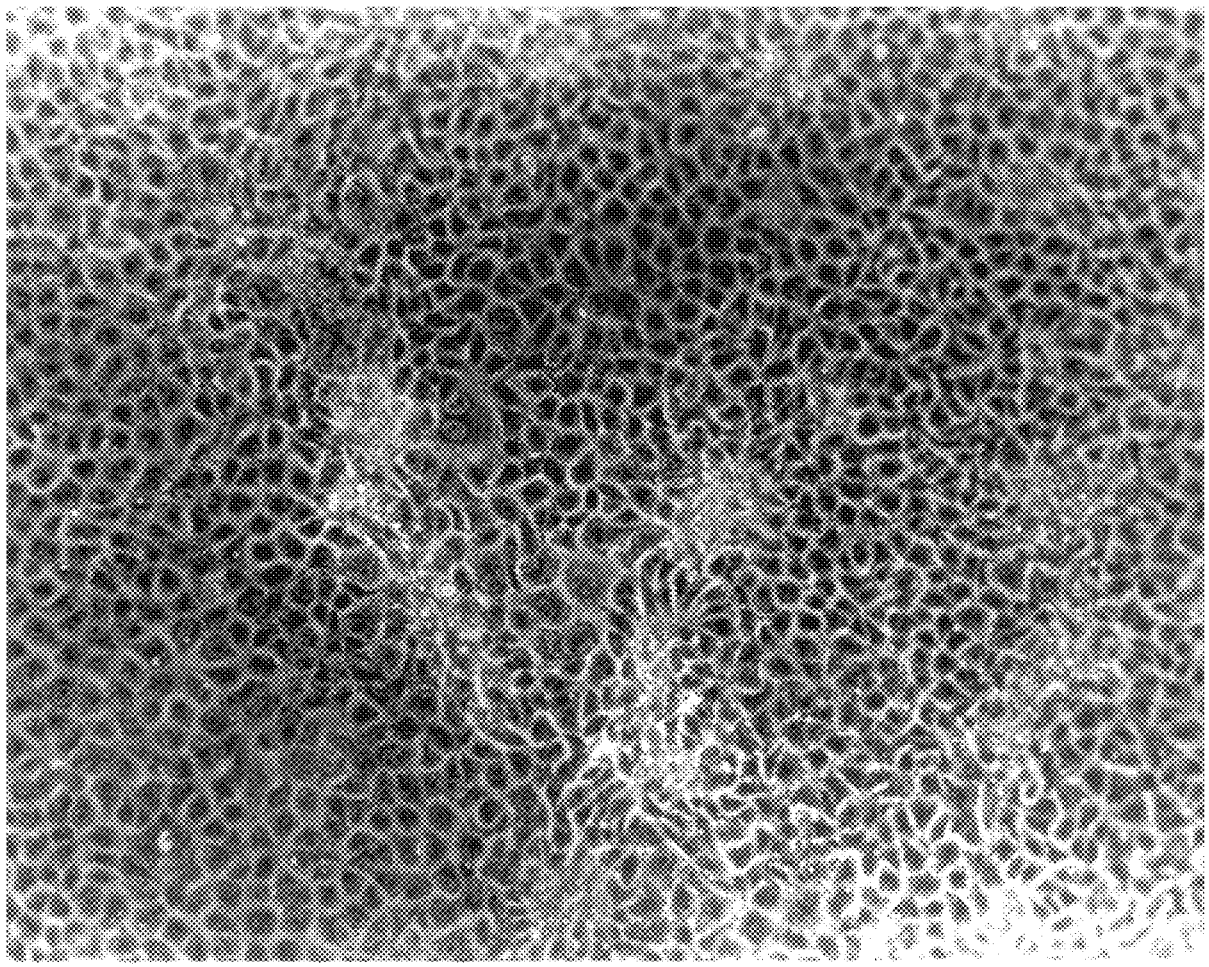
FIG. 4 is a photograph by phase contrast microscopy showing uninfected OMK cells.
Figure 5:
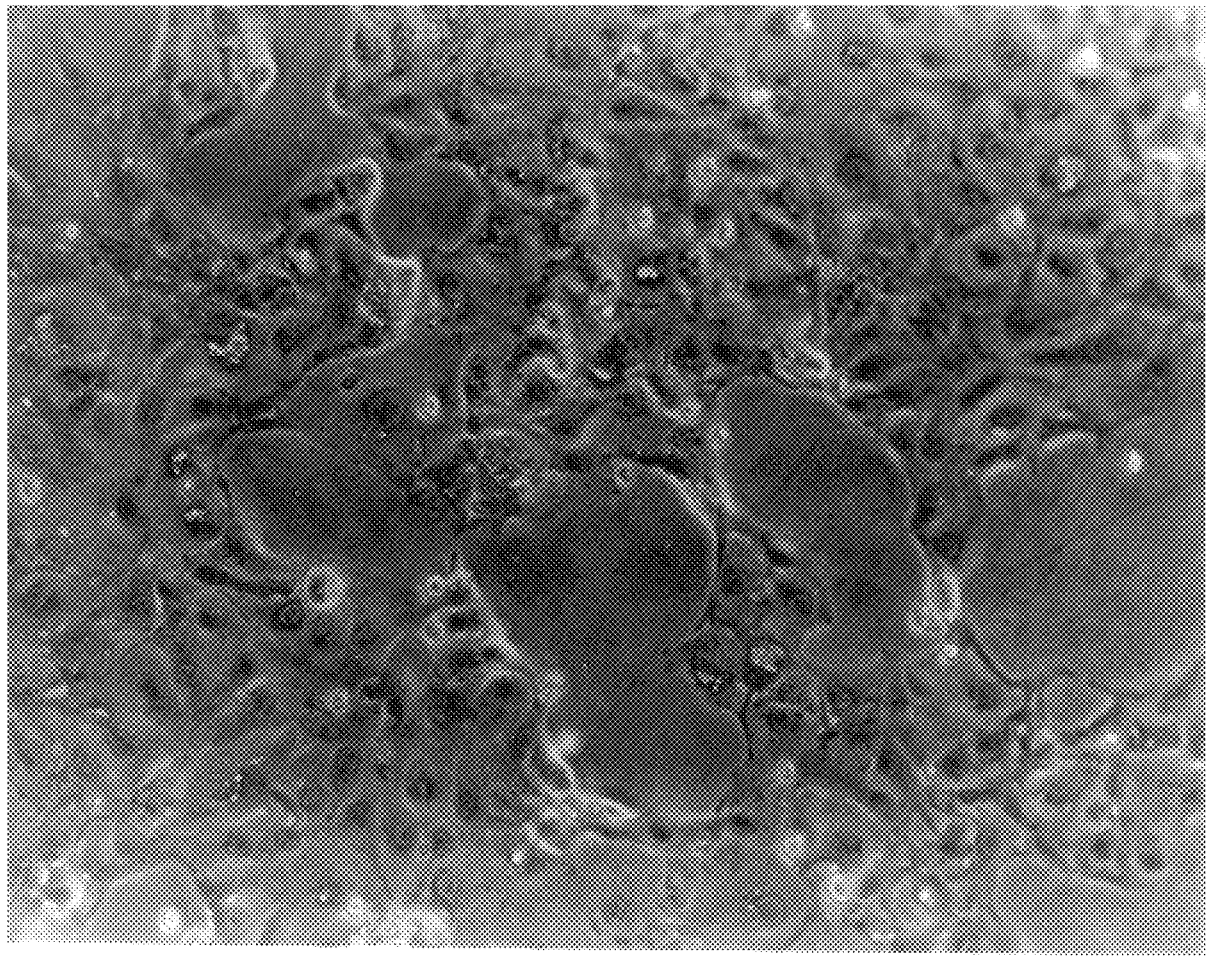
FIG. 5 is an electron micrograph of negatively stained grids from suspensions of activating virus obtained from lymphocyte cultures from wasting marmosets.

Antibodies were obtained from recovered serum and/or ascites fluid of water marmosets by ammonium sulfate exclusion followed by dialysis to remove excess ammonium sulfate. Then Protein A processing followed by biolinylation was used to obtain a "purified marmoset preparation, which was reacted against tissue sections of lymphoid tissue taken from AIDS autopsies, AIDS anatomical athology sectins, normal lymphoid tissues consistent with diseased ones specificaly for monoclonal antibodies isted in Table 4.

Lymphocyte fractions for cell culture or for cocultivation were obtained from fresh heparinized blood by underlaying up to 5 ml of blood in a conical 15 ml centrifuge tube with 10 ml of ficoll-metridazole, density 1.077 (Sigma), and centrifuging at 700 rcf in a swinging-bucket rotor for 40 min. The layer of cells at the interface was removed, diluted with RPMI-1640, and centrifuged at 300 rcf for 10 min. The cell wash was repeated twice.

Cell culture was done by standard methods. Cell lines were grown in disposable tissue culture flasks with the appropriate medium for the cell line, as recommended by the American Type Culture Collection (Rockville, Md.), which was the source of most of the cell lines used. SW-13 and SW-47 cell lines were obtained from Dr. W. McCombs (Scott and White Clinic and Hospital, Temple, Tex.). Typically, RPMI-1640 with HEPES and glutamine was used for lymphoid lines and Eagle's MEM with glutamine (Sigma #MO643) was used for epithelial and fibroblast lines. Unless recommended otherwise by the ATCC, media were supplemented with 10% fetal bovine serum and 1% antibiotic-antimycotic solution. All medium components were usually obtained from Sigma Chemical Co., St. Louis, Mo. Adherent cell lines were split by washing with Hank's solution without calcium and magnesium, incubating with trypsin-EDTA, and suspending the cells in Hank's solution by pipetting. Suspended cells were also used to prepare air-dried smears for immunostaining or were pelleted by centrifugation and fixed for some electron microscope studies with 3% glutaraldehyde-0.05 M phosphate-sucrose (pH 7.2), or with half-strength Karnovsky's fixative (Karnovsky, *J. Cell Biol.,* 17:208, 1963).

For initial studies, antibodies to MAV were obtained from heparinized or clotted blood of marmosets recently recovered from or suffering from marmoset wasting syndrome. Serum or plasma was precipitated twice with 50% saturated ammonium sulfate for 30–45 min and the precipitate was recovered by centrifugation at 700 rcf for 15 min. The precipitate was dissolved in PBS, dialyzed overnight, absorbed on protein-A agarose, and eluted with 0.5% acetic acid—0.15M saline. The protein peak was pooled, dialyzed against PBS, and for direct immunostaining was biotinylated with N-hydroxysuccimidobiotin (Warnke, et al., *J. Histochem. Cytochem.,* 28:771–776, 1980). Aliquots were frozen at −75° C. to −85° C.

In order to produce rabbit anti-marmoset secondary antibody, immunoglobulin was obtained from marmosets and purified as above. Rabbits were immunized with a subcutaneous injection of a mixture of purified immunoglobulins in complete Freund's adjuvant once a week for three weeks. Following a booster dose without adjuvant, the rabbit serum was harvested and purified as above.

A study was done on the ability to propagate the virus in various cell cultures by inoculating the cultures with a homogenate of frozen marmoset autopsy tissues, including spleen, liver, and kidney tissues were homogenized in a glass tissue grinder and filtered through a 0.2 μm membrane. After inoculation, cell lines were observed for cytopathic effects and for antigen production by immunoperoxidase staining.

Cell lines in which MAV growth or antigen production were not observed based on lack of a cytopathic effect and lack of a difference in immunoperoxidase staining between the control and the inoculated cells included HELA, VERO, CCRF-CEM, MRC-5, WI-38, SW-13, SW-47, K562, RPMI-2650, Ramos and NIH-3T3. Raji showed a low level of antigen production by immunoperoxidase.

For immunoperoxidase staining of tissues, routine formalin-fixed, paraffin-embedded sections were deparaffinized in xylene and hydrated through graded alcohols. For staining of smears, air-dried smears were fixed at 60° C. with formalin fumes for 30 min and redried. Endogenous peroxidase activity was blocked with 80% methanol-0.6% hydrogen peroxide for 30 min. The slides were incubated with an appropriate dilution (1:10 to 1:50) of biotinylated marmoset antibody diluted in PBS for 1 hr. The slides were washed in PBS for 15 min. Avidin-biotin-peroxidase complex (Vectastain, Vector Laboratories, Inc., Burlingame, Calif.) was added for 30–45 min (Hsu, et al., *J. Histochem. Cytochem.,* 29:577–580, 1981; Hsu, et al., *Amer. J. Clin. Pathol.,* 80:415–420, 1983). The slides were washed in PBS for 10 min and incubated in 0.075%, 3,3'-diaminobenzidine-0.06% hydrogen peroxide in PBS or 0.1 M Tris-HCl, pH 7.4 for 6 to 10 min. Replacement of the Vectastain by Vectastain Elite permitted higher antibody dilutions, up to 1:500 or more. An indirect immunostaining technique utilizing non-biotinylated marmoset antibody for 1 hr, followed by a rabbit anti-marmoset IG antibody followed by biotinylated anti-rabbit IG antibody, (technical details in Elite Vectastain kit) permitted staining with the marmoset antibody at 1:5000 dilution.

OMK (ATCC #CRL 1556) cultures inoculated in this way developed a subtle cytopathic effect (CPE) in 5–7 days consisting of areas of cells that rounded up and showed increased refractivity, especially at their margins. These changes must be distinguished from the normal differentiation changes which occur with this cell line, which involve areas with differing cell size, cell arrangement, cell granularity, etc. These subtle changes were demonstrated by phase-contrast microscopy, but were difficult to detect by bright-field microscopy. No syncytia or recognizable intracellular inclusions were seen. A low level of cell necrosis occurred in the areas showing cytopathic effects, but lytic plaques did not occur (strain designation Ethel and #65). In contrast, *Herpes ateles* grown under the same conditions produced localized syncytia, intranuclear inclusions, and eventually produced cell lysis, which ultimately lysed all of the cells present in many flasks. Smears from the inoculated OMK cultures showed strong immunoperoxidase staining. The cytopathic effect and antigenicity was transferable by inoculating new OMK cultures with the culture supernatants. Cultures remained productive for several months. Eventually the cell population became depleted. The cytopathic effect is shown in FIGS. 1 and 2. In contrast, FIGS. 3 and 4 show the appearance of uninfected OMK cells. FIG. 5 shows changes developing in long term cultures where foci of lysis did eventually develop, often with small clusters of highly refractile cells at their margins. Intracellular granules are also common in infected cultures, but appear to be relatively less specific.

Virus was next cultured from another marmoset (strain George) by cocultivating the lymphocytes obtained as described above with OMK cells and directly from serum. This marmoset later developed wasting syndrome. Virus was isolated from the serum of an asymptomatic marmoset from the same family group (strain Palmer) and from the serum of 9 other marmosets.

MAV was purified from frozen or fresh cell culture supernatants by thawing and centrifugation at 700 rcf for 10 min in conical 50 ml centrifuge tubes. The supernatants were transferred to high speed 40 ml tubes and 8% polyethylene glycol (m.w. 6000–8000) was dissolved in the supernatant. The virus was pelleted by centrifugation in a JA-20 rotor at 20,000 rpm (31,400 rcf) for 120 min. The pellets were suspended in 0.05 M NaCl-0.05 M Tris-HCl, pH 7.4 and incubated overnight at 4° C. The suspension was underlaid with a step gradient of 20% sucrose and 40% sucrose (later studies used preparations from a gradient of 30% and 45% sucrose) and centrifuged in a JS 13.1 rotor at 13,000 rpm (17,700 rcf) for 120 min. A hazy zone at the interface of the sucrose layers was removed and constituted the virus preparation. Electron microscopy confirmed that virus was present in this zone.

An alternate purification scheme was used for a few experiments. After the initial PEG centrifugation as above, the resuspended pellet was absorbed onto a Matrex Cellufine Sulfate column (Amicon), washed with 0.05 M NaCl-0.05M Tris-HCl, and eluted with increasing concentrations of NaCl in 0.02 M Tris-HCl, pH 7.4. Dot blots indicated that the antigen was eluted at about 2.0 M NaCl concentration. Electron microscopy as described in Example 3 below, demonstrated intact virus particles in the eluate; however, the majority of the material recovered may not have been intact, as there was a considerable increase in antigen activity in the eluate.

EXAMPLE 2

Isolation of Activating Virus Human (HAV) From Human Specimens

Using techniques similar to those described above for MAV, human blood serum samples were tested for the presence of a human activating virus (HAV) analogous to MAV. In initial studies, cultures of OMK cells were inoculated with serum from appropriate subjects and in two instances were cocultivated with lymphocytes, including one typical HIV-I AIDS patient (strain #65), two AIDS patients on AZT therapy (strains MDH and SRG, also cocultivated) one asymptomatic HIV-1 positive patient (strain SM), one African AIDS patient positive for HIV-II (strain #75), an asymptomatic subject negative for HIV, but with a long history of exposure to marmosets and shown to have reactive peripheral blood lymphocytes by immunoperoxidase staining (strain FS), an asymptomatic patient with HTLV-I (strain #120), a patient with chronic lymphocytic leukemia (strain PC) and a patient with breast cancer (strain DB). The HAV was successfully isolated from all these sources. Cultivation from serum seemed to be superior to cocultivation with lymphocytes. The isolates had the same general culture characteristics as the marmoset isolates, although the period until development of cytopathic effect varied from 3–10 days to as long as one month. Several of these isolates proved more difficult to pass than the other human or marmoset isolates, notably those from the AZT-treated patients, but all were successfully passed. The isolations are summarized in TABLE 1.

TABLE 1

HAV ISOLATES OBTAINED FROM CULTURE

| Patient Status | Number of Strains | Strain Designations |
|---|---|---|
| exposed to marmosets with wasting syndrome | 1 | FS |
| asymptomatic HIV-I positive | 1 | SM |
| AIDS, HIV-I positive | 3 | 65, MDH, SRG |
| HIV-II positive | 1 | 75 |
| asymptomatic, HTLV-I | 1 | 120 |
| CLL[a] | 1 | PC |
| lymphoma[b] | 2 | — |
| breast cancer | 1 | DB |

[a]chronic lymphocytic leukemia
[b]not examined by electron microscopy

EXAMPLE 3

Characterization of Activating Virus (Activiron)

Extensive testing was performed establishing the novel nature of AV isolated from marmosets and humans.

A. Electron Microscopy

Studies were done using electron microscopy to characterize MAV. For these analyses, cell pellets were prepared and fixed as above and embedded in Poly/Bed 812 or Araldite, Mollenhauer Medium, Spurr Medium, or LR white (Polysciences, Inc., Warrington, Pa.). Alternatively, cell suspensions were prepared from flask cultures following removal using a sterile spatula and sedimented in a microcentrifuge. All pellets were then fixed and embedded. This latter method appeared to give more satisfactory preparations with less cell damage. Sections were cut with diamond knives, stained with Reynolds' lead citrate (Reynolds, *J. Cell Biol.*, 17:208, 1963) and uranyl acetate, and viewed in a Phillips EM-420 electron microscope.

For negative staining of purified virus, formvar-coated grids (E.M. Sciences, Ft. Washington, Pa.) were floated or immersed for 1–2 hr on marmoset or goat antibody diluted 1:10 to 1:20 with PBS. After washing in PBS, the grids were floated on drops of the purified virus preparations for 1–3 hr. The grids were washed with PBS and floated on 3% glutaraldehyde-0.05 M phosphate-sucrose for 30 min. They were washed in distilled water and floated on 0.5% uranyl acetate or 0.5% phosphotungstic acid for 1–5 min, dried, and viewed as above.

Initial electron microscopy of lymphocyte cultures from wasting marmosets failed to demonstrate any definite viral particles. There was an increase in cytolysosomes and granules containing dense material in the cytoplasm. Monocyte vacuoles contained small, empty, membrane-bound granules. Electron microscopy of infected OMK cells suspended in trypsin-EDTA produced a similar result, except that the endoplasmic reticulum and granules containing dense granular material were more prominent. Irregular profiles with several concentric layers of membrane were also seen. Viral particles were extremely rare. For example, within one cell a single virus-like particle with a small core, an apparent capsid and an envelope was seen within a cytolysosome.

Figure 6:
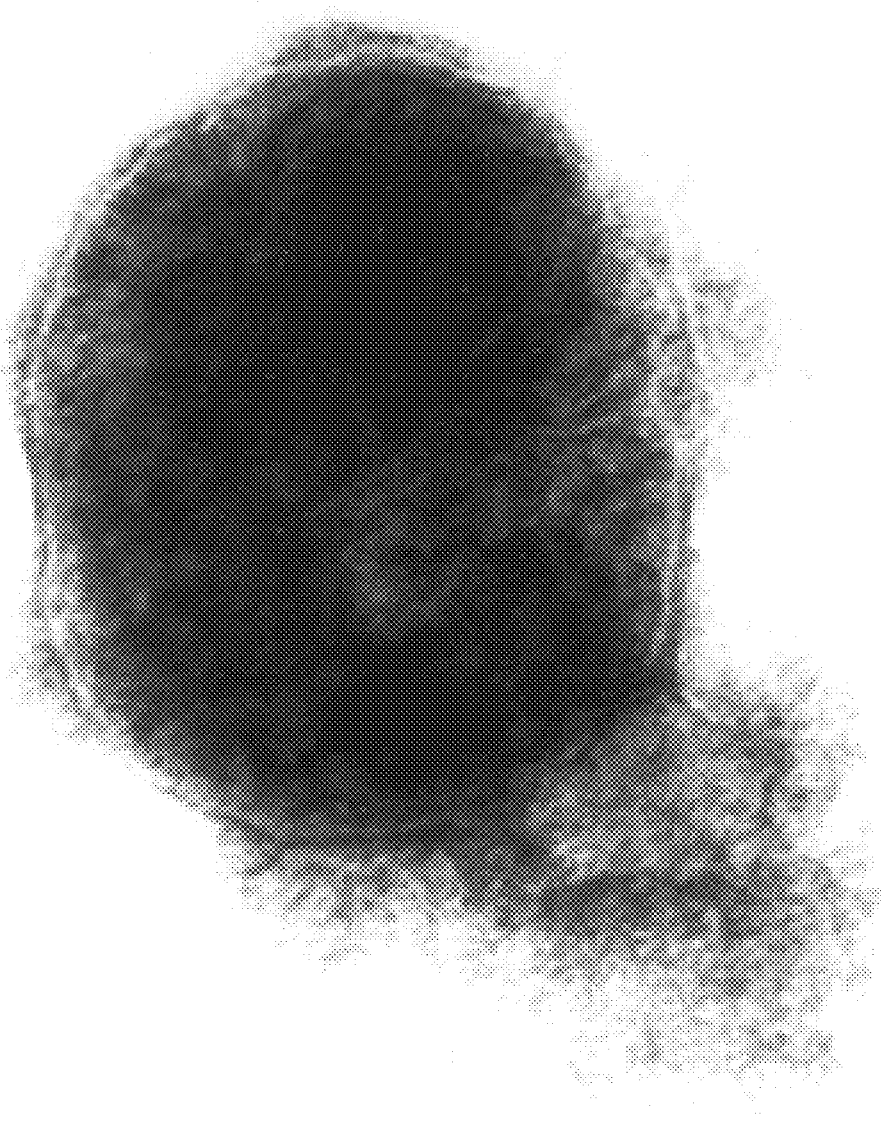
FIG. 6 is an electron micrograph of negatively stained grids from suspensions of activating virus obtained from lymphocyte cultures from wasting marmosets

Negatively-stained grids made from virus suspensions showed virions with a somewhat variable appearance. Many virus-like particles appeared to be incomplete and the internal structure of the particles was difficult to demonstrate due to weak staining contrast. In preparations made from frozen and thawed suspensions, the capsids were generally disrupted, although it was evident that the particles were enveloped with a polygonal shape often apparent. Phosphotungstic acid staining gave a better visualization of internal structure than uranyl acetate. Grids from fresh, unfrozen virus preparations provided a better demonstration of the structure, showing an envelope or coat with a smooth surface, no separation between the envelope and underlying capsid, a semi-regular capsid composed of a varying number of small capsomeres and with an apparently imperfect icosahedral symmetry, and a poorly defined possibly elongated or toroidal core. The dimensions of the particles as shown in FIGS. 5 and 6, ranged from 57 to 364 nm with an average size of slightly less than 100 nm. This appearance excludes most known groups of viruses. There are some general similarities to certain known viruses, especially the Herpesvirus, but there are significant differences in detail between these results and the descriptions of all presently defined mammalian viral genera.

Electron microscopy of sections of infected OMK cells scraped off the surface of the flask and pelleted by centrifugation showed that in most preparations viral particles are extremely uncommon and difficult to find. In a preparation from a marmoset strain that developed very prominent cytopathic effect and cell lysis after long passage in cell culture, viral particles were relatively common. Viral particles were present in both the nucleus and cytoplasm, with the nucleus containing more particles, most of which were unenveloped capsids with or without cores. Enveloping was observed within the nucleus adjacent to the nuclear membrane. In section, the core frequently appeared elongated.

B. Gel Electrophoresis

Additional studies were done on purified AVM by gel electrophoresis to investigate distribution of various proteins. For gel electrophoresis, virus preparations were concentrated by vacuum ultrafiltration or centrifugal ultrafiltration.

Western Blot Analysis, Strain #65

The vertical electrotransfer apparatus was run for two hours at 0.8 mAmps under standard conditions. A 0.45 Nitrocellulose membrane (Hoefer Scientific Instr., San Francisco, Calif.) was used to receive the transferred proteins. Following the transfer, the blot was immunostained according to previously described procedure, using purified biotinylated donkey anti-65 polyclonal antibody at a 1:100 dilution. The staining procedure was completed using standard avidin-biotin complex reagents purchased from Vector Labs (Burlingame, Calif.).

It was possible to compare one dimensional gel electrophoresis of disrupted #65 with a Western Blot procedure. As with the silver stain of #65, estimated molecular weights were established by plotting Rf values of the PAGE versus known MV standards. The results are as follows: Larger polyacrylamide gels were run in a SE600 vertical PAGE apparatus (using the Laemmeli SDS-PAGE technique (Hoefer Scientific Instruments Catalog 1988–1989, pp 131–134, Hoefer Scientific Instruments, San Francisco, Calif.; Laemmeli, *Nature,* 227:680–85, 1970).

Major bands were demonstrated at molecular weights of 58,800; 48,000, 44,000, and 32,000, respectively. A distinct bind was demonstrated at 106,500 with the remaining bands being faintly distinct.

SDS-PAGE Analysis, Strain #65

SDS-polyacrylamide gel electrophoresis was done using the PHAST™ system (Pharmacia-LKB, Piscataway, N.J.) and precast Phastgels and buffer strips, following the normal running procedures for the gels (PhastSystem Owner's Manual, Pharmacia LKB Biotechnology, Inc., Piscataway, N.J., 1986) according to Laemmeli, using an 8.0% separation gel with a 4.0% stacking gel. The vertical electrophoresis was run under standard conditions for three hours at 150 mAmps. The gel was then silver stained and photographed. Standard molecular weights purchased from Sigma were biotinylated according to standard procedures, with a 0.1 mg/ml concentration and a similar concentration for disrupted strain #65. Gel thickness was kept at 1.5 mm per poured gel (AMRESCO, Solon, Ohio). Six molecular weight standards were used. They were myosin, beta-galactosidase, phosphorylase B, bovine plasma albumin, egg albumin and carbonic anhydrase with weights at 205,000, 116,000, 97,400, 6,000, 45,000, and 29,000 daltons, respectively.

Gels were stained with Pharmacia-LKB silver staining kit (PhastGel Silver Kit Instruction Manual, Pharmacia LKB Biotechnology, Inc., Piscataway, N.J., 1987) or blot transfers to nitrocellulose were prepared. These blots were later stained with india ink or immunostained. For immunostaining, the free binding sites were blocked with 0.05% Tween-20—0.1% BSA and then immunoperoxidase stained using the reagents described above for tissue immunostaining with appropriate adjustments in the antibody dilutions and incubation times.

Figure 8:
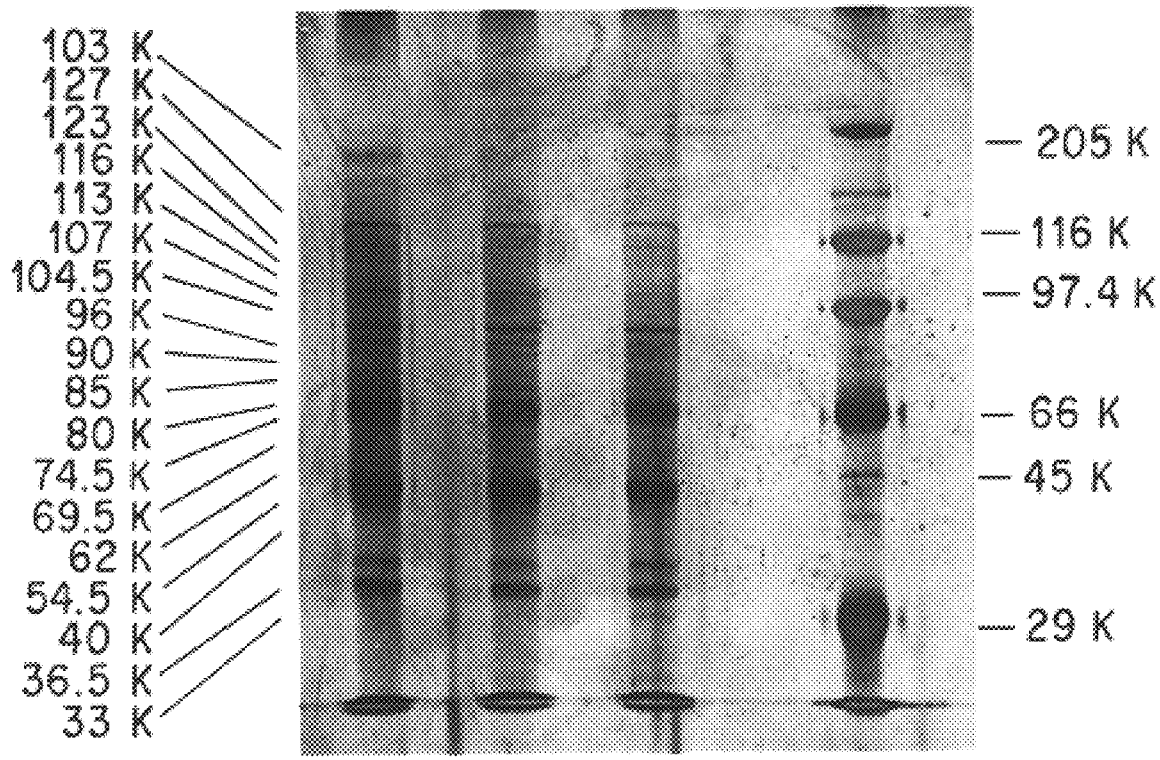
FIG. 8 is a photograph of a silver stained gel after vertical electrophoresis of human activating virus (strain #65).

Preliminary results of SDS-PAGE electrophoresis on concentrated purified virus show at least 18 bands, illustrated in FIG. 8. Total Tracking Distance for Silver stain was 82 mm, while total tracking distance used for Western Blot was 77 mm. Therefore, at higher MW calculations, some disparity is likely to be observed. There is close correlation with MW's at 168/163; 127/126.8; 107/106.5; 96/95 and 33/32. Direct correlation occurs at 80 and 74.5, respectively. The observed variation is likely due to measurement error of Rf value versus known MW standards as demonstrated here. The approximate molecular weights are given in Table 2.

TABLE 2

| Silver Stain Analysis | Western Blot Analysis |
|---|---|
| 163,000 | 198,000 |
| 127,000 | 168,000 |
| 123,000 | 126,800 |
| 116,000 | |
| 113,000 | |
| 107,000 | 106,500 |
| 104,500 | |
| 96,000 | 95,000 |
| 90,000 | |
| 85,000 | |

TABLE 2-continued

| Silver Stain Analysis | Western Blot Analysis |
|---|---|
| 80,000 | 80,000 |
| 74,500 | 74,500 |
| 69,500 | |
| 62,000 | |
| | 58,800 |
| 54,500 | |
| | 48,000 |
| 46,000 | |
| | 44,000 |
| 36,500 | |
| 33,000 | 32,000 |
| | 30,500 |
| | 26,000 |

C. Reverse Transcriptase

Reverse transcriptase was assayed on culture supernatants and purified MAV virus was directly pelleted from the supernatants by ultracentrifugation for 1.5 hr. Virus was pelleted by initially diluting the purified virus preparation to reduce the sucrose content followed by ultracentrifugation. The pellet was resuspended in ⅒oth of the original volume of 10 mM Tris-HCl (pH 7.9)—1 mMEDTA-200 mM KCl—10 mM betamercaptoethanol—3 μM leupeptin-0.5% Triton X-100, dispersed by vortexing, and kept at room temperature for 1 hr. 10 μl of the sample was assayed in a final volume of 50 μl containing 60 mM Tris-HCl (pH 7.9), 0.07% Triton X-100, 7 mM $MgCl_2$ or 0.6 mM $MnCl_2$, 20 μg/ml of poly(rA)-p(dT) (Marczynska, et al., *Infect. Immun.*, 31:1261–1269, 1981; Roizman B, ed. *The Herpesviruses*, Plenum Press, New York, N.Y., 1982; Salahuddin, et al., *Science*, 234:596–601, 1986; Fox, et al., *Lancet*, 2:396, 1988; and 6 μM dTTP (41.6 Ci $^3$H/mmole). The reaction mixtures were incubated at 37° C. for 1 hr, terminated by the addition of sodium pyrophosphate. Aliquots were precipitated onto glass fiber filters and batch washed with 5% trichloroacetic acid, ethanol, and acetone. The filters were dried and counted for radioactivity. Authentic HIV-I reverse transcriptase was run in each experiment as a positive control. Assays were run in quadruplicate.

$Mg^{++}$ dependent reverse transcriptase, typical of HIV and most other defined human retroviruses, was absent from all samples. A $Mn^{++}$ dependent reverse transcriptase was identified in the culture supernatants from both the virus producing cultures and the uninoculated cell line, but was absent from the purified virus. This implies that the cell line may contain an undefined retrovirus, probably in the group causing soft tissue tumors.

D. Susceptibility to Nuclease

Several experiments were performed using nucleuses to determine the nucleic acid content of MAV. The viral genome was digested using 4–10 units of DNAse I (Sigma; in 10 mM MnCl, 50 mM Tris Cl, pH 7.5, 50 μg/mL BSA), RNAse A (Sigma; in 10 mM Tris Cl, pH 7.5, 300 mM NaCl, 5 μM EDTA) or S 1 Nuclease (Sigma; 50 mM Na Acetate, pH 4.5, 1 mM Zinc Acetate, 0.25 M NaCl, 0.5 mg/mL BSA) in a total volume of 50 μL. Each reaction tube contained 4 μg of viral nucleic acid.

The reaction tubes were incubated for 1 hr at 37° C. Phenol extraction of the mixtures was followed by ethanol precipitation at −20° C. overnight. The nucleic acid was pelleted by centrifugation (14,000×G) and resuspended in 100 μL of TE buffer (10 mM Tris-HCl, pH 7.4 and 1 mM EDTA). The digestion reactions were analyzed using 0.7% agarose gel electrophoresis. The undigested viral genome extract yielded one band migrating at an apparent MW of 20 kilobases (kb) and a low MW smear presumably of degraded nucleic acids. DNase I digestion resulted in the complete degradation of the fragment. RNase A digestion had no visible effect on the band profile. S 1 Nuclease digestion decreased the size of the 20 kb fragment by approximately 0.5 kb, and the smear of nucleic acids on the profile was completely degraded.

E. Reactivity of Anti-MAV (strain Ethel) and Anti-HAV (strain #65) With Various Viruses Dot blots were prepared by pipetting samples onto 0.20 μm nitrocellulose membrane (Pharmacia, Hoefer) and allowing them to absorb overnight at 4° C. Typically, samples with a protein concentration of 10 μg/ml in PBS were used and the sample aliquot pipetted on the membrane were 100 μl/dot. Each membrane was then blocked with an 80:20 solution of methanol:peroxide (3%) and followed with 3 washes of 0.1 M Tris, pH 7.2, 0.1% BSA and 0.05% Tween-20 for 30 min while rotating. Antibody concentrations were always 30 μg/ml for this type of assay. The detection antibody was diluted to be at least three times the concentration of absorbed antigen(s) and allowed to incubate at room temperature for at least 2 hr. The membrane was washed, and ABC (Vector) was applied for 45 min at room temperature, washed, and incubated with DAB/Tris until color development was noted. The reaction was stopped using water, and membranes were allowed to dry at room temperature. Viruses tested for reactivity with antibodies to activating virus (AV) are listed in TABLE3.

TABLE 3

VIRUSES TESTED WITH ANTI-AV

| ATCC# | Strain | Description of Viral Strain |
|---|---|---|
| vr-2002 | SB | Marek's disease (Avian HV) |
| vr-585 | JM | Marek's disease (Avian HV II) |
| vr-631 | DN-589 | Bovine HV |
| vr-552 | D-004 | Canine HV |
| vr-665 | Auburn 1 clone | Channel catfish HV |
| vr-636 | C-27 | Feline HV |
| vr-603 | HR-1 | Burkitt's Lymphoma (Epstein-Barr) |
| vr-977 | Towne | Cytomegalovirus |
| vr-260 | HF | Herpes simplex 1 |
| vr-734 | G | Herpes simplex 2 |
| vr-795 | Oka | Varicella |
| vr-586 | Ellen | Varicella zoster |
| vr-606 | S-34e | Herpesvirus aotus |
| vr-349 | MV-5-4 | Herpesvirus platyrhinnae |
| vr-607 | S-338 D | Herpesvirus saguinus |
| vr-608 | S-295 C | Herpesvirus saimiri |
| vr-677 | 68-1 | Rhesus CMV |
| vr-706 | CSG | Vervet CMV |
| vr-928 | Unknown | Squirrel monkey CMV |
| vr-568 | Rafferty | Frog virus 4 (Lucke tumor) |
| vr-837 | BK virus | Human polyoma virus |
| vr-819 | MAD-1 (JC virus) | Human polyoma virus |
| vr-305 | A-2895 | SV-40 |
| vr-806 | GB | Hepatitis A (marmoset) |
| CRL 168 | FRhK-4 | Hepatitis A (rhesus) |
| vr-908 | Fujinami | Fujinami sarcoma (helper virus) |
| vr-335 | RAV-1 | Rous associated virus A (Avian leukosis A) |
| vr-658 | RAV-2 | Rous associated virus B (Avian leukosis B) |
| vr-727 | RAV-49 | Rous associated virus C (Avian leukosis C) |
| vr-660 | RAV-50 | Rous associated virus D (Avian leukosis D) |
| vr-751 | RAV-60 | Rous associated virus E (Avian leukosis E) |
| vr-334 | Bryan | Rous sarcoma |
| vr-721 | FL-237 | Feline leukemia virus |
| vr-717 | MAH | Feline leukemia virus |
| vr-595 | B/T-L | Murine leukemia virus |

TABLE 3-continued

VIRUSES TESTED WITH ANTI-AV

| ATCC# | Strain | Description of Viral Strain |
|---|---|---|
| vr-596 | Br-Bc | Murine leukemia virus |
| vr-844 | Moloney | Murine sarcoma virus |
| vr-655 | Ls-13 | Bovine syncytial virus |
| vr-732 | Unknown | Mouse mammary tumor virus |
| vr-731 | GR | Mouse mammary tumor virus |
| vr-940 | Hooks 40 | Simian foamy virus type 8 (Ateles spp) |
| vr-919 | FXV | Syncytium forming virus of marmosets |

[a]anti-MAV and anti-HAV

In each instance, appropriate negative and positive controls were run. Although weak reactivity (+/−) was seen with ATCC vr 585, 595, and 731, no reaction was detected with any of the other viruses showing that the AV is distinct from all the viruses tested.

F. Reactivity of Antibody Specific for Various Viruses With MAV (strain Ethel) and HAV (strain 65)

Monoclonal antibodies to various known viruses (Chemicon, Inc., Temecula, Calif.; Pan-Data, Boulder, Colo.) in either purified or ascites form, were used to measure reactivity with disrupted virions of MAV (strain Ethel) and HAV (strain 65). TABLE 4 lists monoclonal antibodies that were tested.

TABLE 4

VIRAL MONOCLONAL ANTIBODIES TESTED WITH MAV AND HAV

| VIRUS RECOGNIZED | ANTIGEN | VIRUS RECOGNIZED | ANTIGEN |
|---|---|---|---|
| adenovirus | — | RSV | pan |
| corona | Gp | HTLV-1 | p19 |
| CMV | early | HTLV-1 | p41 |
| CMV | late (68kD) | HIV-1 | p17 |
| EBV | capsid | HIV-1 | p24 |
| EBV | nuclear | HIV-1 | gp120/160 |
| hepatitis A | — | HHV-6 | p41 |
| HSV-1 | — | HHV-6 | gp82 |
| HSV-2 | — | HHV-6 | gp120 |
| VZV | — | HHV-6 | gp116 |

In addition to testing with MCA's to the viruses noted in TABLE 4, AV viral strain Ethel, 65, and FS, were tested in commercially available kits by ELISA (hepatitis B core antigen, hepatitis B surface antigen, HIV-1, HIV-2) and by Western blot (HIV-1, HIV-2, HTLV-1). In these studies, none of the MCA's specific for known viruses was reactive either with HAV or MAV.

Activating virus strain Ethyl, ATCC Accession No. VR2257 and activating virus strain #65, ATCC Accession No. VR 2256 were deposited on Dec. 28, 1989 at American Type Culture Collection, Rockville, Md. 20852.

EXAMPLE 4

Western Blot Analysis, Strain #65

The SDS-PAGE of strain #65 HIV obtained as described above was electroblotted using a Pharmacia (Piscataway, N.J.) vertical electrotransfer apparatus for 2 hours at 0.8 mAmps under standard conditions. A 0.45 Nitrocellulose membrane (Hoefer, Scientific Instruments, San Francisco, Calif.) was used to receive the transferred proteins. Following the transfer, the blot was immunostained according to previously described procedure, using purified biotinylated donkey anti-65 polyclonal antibody at a 1:100 dilution. The staining procedure was completed using standard avidin-biotin complex reagents purchased from Vector Labs (Burlingame, Calif.). The substrate used was horseradish peroxidase.

Standard molecular weights ladders (Sigma, St. Louis, Mo.) were biotinylated according to established procedures. Therefore, it was possible to compare one dimensional gel electrophoresis of disrupted #65 with a Western blot procedure. As with the Silver stain of #65 (TABLE 2), estimated molecular weights were established by plotting Rf values of the PAGE versus known MW standards. The results are shown in TABLE 5 below.

TABLE 5

| Tracking Distance | Rf Value | Molecular Weight |
|---|---|---|
| WESTERN BLOT #65 | | |
| 11 mm/77 mm | 0.14 | 198 K |
| 13.5 mm/77 mm | 0.18 | 168 K |
| 19.5 mm/77 mm | 0.25 | 126.8 K |
| 23 mm/77 mm | 0.30 | 106.5 K |
| 25.5 mm/77 mm | 0.33 | 95 K |
| 29.5 mm/77 mm | 0.38 | 80 K |
| 31 mm/77 mm | 0.40 | 74.5 K |
| 36 mm/77 mm | 0.47 | 58.8 K |
| 41 mm/77 mm | 0.53 | 48 K |
| 43.5 mm/77 mm | 0.56 | 44 K |
| 51.5 mm/77 mm | 0.67 | 32 K |
| 53.5 mm/77 mm | 0.69 | 30.5 K |
| 58 mm/77 mm | 0.75 | 26 K |
| STANDARD VALUES | | |
| 10 mm/77 mm | 0.13 | 205 K |
| 21 mm/77 mm | 0.27 | 116 K |
| 27 mm/77 mm | 0.35 | 97.4 K |
| 36 mm/77 mm | 0.47 | 66 K |
| 41.5 mm/77 mm | 0.54 | 45 K |
| 53.5 mm/77 mm | 0.69 | 29 K |

Figure 7:
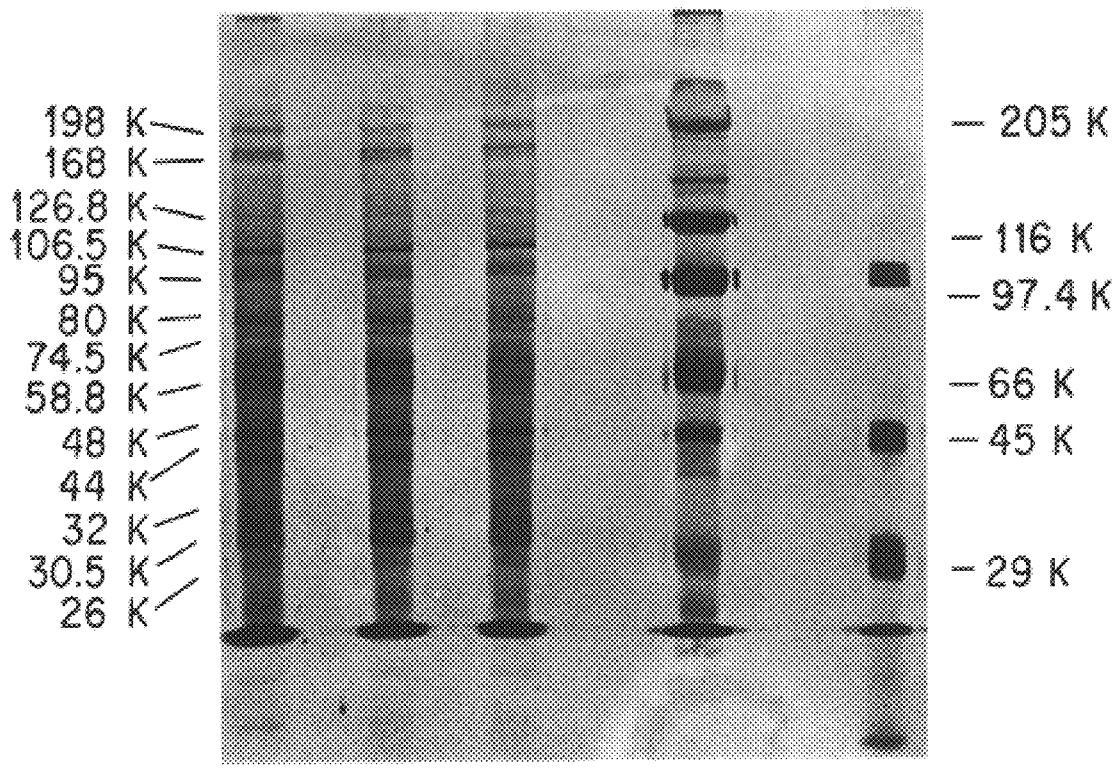
FIG. 7 is an immunograph of an SDS-PAGE Western blot analysis of human activating virus (strain #65).

As shown in FIG. 7, major bands were demonstrated at molecular weights of 58,800; 48,000; 44,000 and 32,000, respectively. A distinct band was demonstrated at 106,500 with the remaining bands being faintly distinct. TABLE 2 compares the silver stain results with Western blot analysis.

EXAMPLE 5

SDS-PAGE Analysis of Strain #65

Purified HAV, strain #65, was analyzed by SDS-PAGE according to Laemmle, using an 8.0% separation gel with a 4.0% stacking gel. The vertical electrophoresis was run under standard conditions for three hours at 150 mAmps. The gel was then silver stained and photographed. Molecular weight standards (Sigma, St. Louis, Mo.) were prepared in the usual manner for this procedure (0.1 mg/ml) and a similar concentration for disrupted strain #65. Gel thickness was kept at 1.5 mm per poured gel (AMRESCO, Solon, Ohio). The results are shown in TABLE 6 below.

Six molecular weight standards were used: myosin, Betagalactosidase, phosphorylase B, Bovine plasma albumin, Egg albumin and Carbonic anhydrase with weights at 205,000, 116,000, 97,400, 66,000 45,000 and 29,000 daltons, respectively. Estimated molecular weights of AAV (as shown in FIG. 8) were calculated by means of Rf value versus known MW standards.

TABLE 6

| Tracking Distance | Rf Value | Molecular Weight |
|---|---|---|
| SILVER STAIN #65 SDS PAGE | | |
| 14.5 mm/82 mm | 0.18 | 163 K |
| 21 mm/82 mm | 0.26 | 127 K |
| 22.5 mm/82 mm | 0.27 | 123 K |
| 23.5 mm/82 mm | 0.29 | 116 K |
| 24.5 mm/82 mm | 0.30 | 113 K |
| 26 mm/82 mm | 0.32 | 107 K |
| 27 mm/82 mm | 0.33 | 104.5 K |
| 30 mm/82 mm | 0.36 | 96 K |
| 31.5 mm/82 mm | 0.38 | 90 K |
| 32.5 mm/82 mm | 0.40 | 85 K |
| 34.5 mm/82 mm | 0.42 | 80 K |
| 36 mm/82 mm | 0.44 | 74.5 K |
| 38 mm/82 mm | 0.46 | 69.5 K |
| 40 mm/82 mm | 0.49 | 62 K |
| 43 mm/82 mm | 0.52 | 54.5 K |
| 46 mm/82 mm | 0.56 | 46 K |
| 52 mm/82 mm | 0.63 | 36.5 K |
| 54.5 mm/82 mm | 0.66 | 33 K |
| STANDARD VALUES | | |
| 12.5 mm/82 mm | 0.15 | 205 K |
| 23 mm/82 mm | 0.28 | 116 K |
| 29.5 mm/82 mm | 0.36 | 97.4 K |
| 39.5 mm/82 mm | 0.48 | 66 K |
| 45 mm/82 mm | 0.55 | 45 K |
| 58 mm/82 mm | 0.71 | 29 K |

EXAMPLE 6

Testing With Human Clinical Specimens

A. Reactivity of Patient Sera With HAV

Corning E-Z wash microtiter 96 well plates and Corning (New York, N.Y.) flat bottom microtiter standard tissue culture 96 well plates were used for solid phase absorption of purified, disrupted viral antigen (strain 65). Approximately 0.400 mg of total viral antigen in 0.05 M PBS, pH 7.2 and disrupted by diluting to a protein concentration of 10 µg/ml. 0.1% sodium dodecyl sulphate (w/v) (Sigma, St. Louis, Mo.). After approximately 1 hr of mixing, 100 µl of disrupted viral protein was pipetted into each microtiter well, with the exception of well A1, which was not filled with any solution and used to blank the entire plate. The plate was stored at 4° C. for 3 days, after which the contents of each well were aspirated. A blocking solution (350 µl) consisting of 0.1 M Tris, pH 7.2, 0.1% BSA and 0.05% Tween-20 (Sigma) was pipetted into each well except A1, and incubated for 3 days at 4° C. Plates were aspirated and either used immediately or frozen in a plastic bag at −85° C. until used.

Alteratively, microtiter plates were prepared as above, but disrupted viral protein was allowed to absorb for 24 hr at 4° C., aspirated, and 350 µl of Superblock (Pierce, Rockford, Ill.) applied to each well for 30 min at room temperature, after which time the plate was aspirated and immediately used.

After each plate had been blocked for non-specific protein activity, 100 µl of a 1:50 serum:PBS clinical sample was pipetted into each experimental well. At least two positive controls and at least three negative controls were used for each plate assayed. The positive control was serum from a known virus carrier, and the negative control was from a known virus-negative serum sample. All controls were run at the same dilutions as experimentals (1:50). The standard time for the primary incubation was typically 90 min at 35° C. Following the conclusion of the primary incubation, all wells were washed 5 times with either a manual plate washer, or an automated plate washer (Bio-Rad, Richmond, Va.). Wells were then filled with 100 µl of monoclonal secondary antibody, which was either mouse anti-human IgG undiluted (Ortho Diagnostics, Raritan, N.J.) conjugated to horseradish peroxidase, or a mouse anti-human IgG conjugated to alkaline phosphatase (Sigma, clone GG-5) diluted (1:2000) in 2% normal mouse serum (Sigma, St. Louis, Mo.), 0.1% Tween-20, and 0.05M PBS, pH 7.2, and incubated for 90 min at 35° C. Following the conclusion of the secondary incubation, the wells were aspirated, washed as before, and 100 µl of substrate applied. For horseradish peroxidase (HRPO), 3 mg of o-phenylenediamine (OPD) per ml of distilled water, 0.05% of 3% hydrogen peroxide was used; for alkaline phosphatase (AP), 1 mg of para-nitrophenyl phosphate (pNPP) per ml of diethanolamine buffer was used. Plates were allowed to incubate at room temperature for 30–45 min or until color development was adequate for detection. 6N sulfuric acid was used to stop the HRPO reaction, and 4M sodium hydroxide was used to stop the AP reaction. Optical density was then measured using either an Ortho reader (492 nm/630 nm) or a Genetics Systems reader (405 nm/630 nm). Readings greater than twice the absorbance of the control wells in experimental wells were considered positive.

The results of these screening tests as shown in TABLE 7 below show that the cells of many cancers suspected of having viral etiology harbor the activating virus of this invention.

TABLE 7

REACTIVITY OF HUMAN SERUM SAMPLES WITH HAV[a]

| DISEASE/AGENT | REACTIVITY[b] |
|---|---|
| AIDS (HIV-I) | 20/20 |
| HIV-1 positive (non-AIDS) | 131/154 |
| HIV-2 (AIDS) | 1/1 |
| HTLV-I (asymptomatic) | 96/122 |
| STD (syphilis positive) | 3/12 |
| Osteosarcoma | 18/18 |
| Liposarcoma | 2/2 |
| Fibrosarcoma | 2/2 |
| Rhabdomyosarcoma | 1/1 |
| Breast Carcinoma | 17/27 |
| Hodgkin's Lymphoma | 19/31 |
| Acute Myelogenous Leukemia | 12/19 |
| Acute Lymphocytic Leukemia | 6/19 |
| Normal | 14/372 |

[a]strain 65
[b]no. positive/no. tested

B. Reactivity of Anti-HAV With Various Malignant Cell Lines

Tumor cell lines were purchased from the American Type Culture Collection (Rockville, Md.). Each line was grown in cell culture in our laboratory according to ATCC specifications. Tissue culture supernatants were collected after each cell feeding and stored at −85° C. until purification as described above for Ethel and strain 65. Purified material was evaluated for antigen identification by dot blot assay.

In performing the dot blot assays, nitrocellulose membranes, 0.22µ (Pharmacia, Hoefer), were used. A circle was inscribed using a #2 lead pencil and 10 µl of sample (20 µg/µl) was pipetted onto the membrane and allowed to dry at room temperature. The membrane was stored at 4° C. or used immediately. Each membrane was washed with an 80:20 mixture of methanol:3% peroxide for 30 min to block endogenous peroxidase activity, followed by a blocking solution of 0.1M Tris, pH 7.2, 0.1% BSA, 0.05% Tween-20 (Sigma), which was applied in three consecutive washes of 20 min each, at room temperature while rotating, to prevent non-specific protein activity. Donkey anti-Ethel or donkey anti-65 biotinylated polyclonal antibody (3 μg/100 ml PBS, pH 7.2) was applied for 1 hr at room temperature while rotating. The membrane was washed 3× with blocking solution and then an avidin-biotin complex (peroxidase) (Vector Laboratories, Burlingame, Calif.) was applied for 45 min at room temperature while rotating. The membrane was washed 3×, substrate added (0.04% 3,3'diaminobenzidine, 0.015% hydrogen peroxide in 0.1 M Tris, pH 7.5) and allowed to stand until color development occurred. The reaction was stopped using distilled water. Positive control was purified AVH (strain 65). Negative control was normal serum of antibody host species, normal human sera, and material purified from uninoculated OMK cells. Results are shown in TABLE 8 below.

TABLE 8

| CELL/TUMOR LINE | ATCC# | CLASSIFICATION |
|---|---|---|
| Carcinomas | | |
| MCF-7 | HTB-22 | Breast |
| MDA-MB-330 | HTB-127 | Breast |
| MDA-MB-134-VI | HTB-23 | Breast |
| BT-474 | HTB-20 | Breast |
| BT-483 | HTB-121 | Breast |
| MDA-MB-361 | HTB-27 | Breast |
| BT-20 | HTB-19 | Breast |
| NCI-H128 | HTB-120 | Lung (small cell) |
| SW-13 | CCL-105 | Adrenal cortex (adeno) |
| Leukemias | | |
| CCRF-HSB-2 | CCL-120.1 | T-cell lymphoblasic |
| H33HJ-JA1 | CRL-8163 | IL-2 producing |
| Mo-T[a] | CRL-8066 | T-lymphocyte, hairy cell var. (HTLV-2 genome) |
| Mo-B[a] | CCL-245 | B-lymphoblast, hairy cell var. (HTLV-2 genome) |
| IM-9 | CCL-159 | Multiple myeloma |
| HuT-78 | TIB-161 | T-cell |
| Molt-3 | CRL-1552 | Acute lymphoblastic |
| Molt-4 | CRL-1582 | ALL |
| Hel 92.1.7 | TIB-180 | Erythroleukemia |
| THP-1 | TIB-202 | Acute monocytic |
| HL-60 | CCL-240 | Promyelocytic |
| ARH-77 | CRL-1621 | Plasma cell |
| K-562 | CCL-243 | Chronic myelogenous |
| KG-1 | CCL-246 | Acute myelogenous |
| CCRF-SB | CCL-120 | Lymphoblastic |
| U-266 | TIB-196 | Myeloma |
| CCRF-CEM[a] | CCL-119 | Acute lymphoblastic |
| Lymphomas | | |
| Ramos | CRL-1596 | African Burkitt's |
| Jijoye | CCL-87 | Burkitt's |
| U-937 | CRL-1593 | Diffuse histiocytic |
| HS-445 | HTB-146 | Hodgkin's |
| Hut-102[a] | TIB-162 | Cutaneous T-cell (HTLV-1 genome) |
| MLA-144 | TIB-201 | IL-2 (Gibbon ape) |
| Raji | CCL-86 | Burkitt's |
| H-9 | HTB 176 | T-cell lymphoma, human |
| Sarcomas | | |
| BL-3 | CRL-8037 | Lymphosarcoma (Bovine) |
| 143-B | CRL-8303 | Osteosarcoma, tk− |
| 143B PML BK TK | CRL-8304 | Osteosarcoma, tk+ |
| MG-63 | CRL-1427 | Osteosarcoma |

TABLE 8-continued

| CELL/TUMOR LINE | ATCC# | CLASSIFICATION |
|---|---|---|
| HOS | CRL-1543 | Osteosarcoma |
| KHOS/NP | CRL-1544 | Osteosarcoma |
| U-2 OS | HTB-96 | Osteosarcoma |
| SK-ES-1 | HTB-86 | Osteosarcoma |
| SAOS-2 | HTB-85 | Osteosarcoma |
| Other Tumor Lines | | |
| Y-79 | HTB-18 | Retinoblastoma |
| WERI-Rb-1 | HTB-169 | Retinoblastoma |
| NB41A3 | CCL-147 | Neuroblastoma (murine) |
| SK-N-MC | HTB-10 | Neuroblastoma |
| LM(TK−) | CCL-1.3 | Connective tissue (BUdR resistant, murine) |
| TK−, ts13 | CRL-1632 | Thymidine kinase temperature sensitive mutant (hamster) |
| A + T-20 | CCL-89 | Pituitary |

[a]HAV was isolated from these tumors

As shown in TABLE 8, this study cell line HS-445, a Hodgkin's lymphoma, was weakly positive. All other cell lines were positive with both anti-MAV (strain Ethel) and anti-HAV (strain 65). In addition, HAV was isolated from cultures of Mo-T, Mo-B, CCRF-CEM, Hut-102, and H-9, showing that AV is associated with cancerous cells.

The foregoing description of the invention is exemplary for purposes of illustration and explanation. It should be understood that various modifications can be made without departing from the spirit and scope of the invention. Accordingly, the following claims are intended to be interpreted to embrace all such modifications.

What is claimed is:

1. An isolated and purified marmoset or human activating virus (MAV or HAV) having the following characteristics: (1) a double-stranded DNA genome; (2) an average diameter of 100 nm as determined by electron microscopy; (3) a spherical capsid with imperfect icosahedral symmetry; (4) a buoyant density of 1.12–1.20 as determined by sucrose gradient centrifugation; (5) major antigens of 32, 44, 48, 58.8, and 106.5 kDa as determined by Western blot analysis and silver staining of SDS-PAGE-resolved proteins obtained from MAV- or HAV-infected OMK cell lysates; (6) minor antigens of 26, 30.5, 74.5, 80, 95, 126.8, 168, and 198 kDa as determined by Western blot analysis and silver staining of SDS-PAGE-resolved proteins obtained from MAV- or HAV-infected OMK cell lysates; (7) a replication deficiency in HELA, VERO, CCRF-CEM, MRC-5, WI-38, SW-13, SW-47, K562, RPMI-2650, Ramos, and NIH-3T3 cell lines as it applies to MAV; (8) replication competence in OMK cell cultures as it applies to both MAV and HAV; and (9) the absence of $Mg^{2+}$-dependent reverse transcriptase activity.

2. A biologically pure culture of marmoset activating virus (MAV) strain Ethyl (ATCC Accession No. VR 2257).

3. A biologically pure culture of human activating virus (HAV) strain #65 (ATCC Accession No. VR 2256).

4. An immunogenic composition comprising the activating virus of claim 1.

5. An isolated and purified cell line stably infected with the activating virus of claim 1.

* * * * *